United States Patent [19]
Wiggins et al.

[11] Patent Number: 6,037,116
[45] Date of Patent: *Mar. 14, 2000

[54] COMPOSITIONS COMPRISING BETAINE, SODIUM CITRATE AND SODIUM CHLORIDE AND METHODS FOR THE PRESERVATION OF BIOLOGICAL MATERIALS

[75] Inventors: Philippa M. Wiggins; Alexander B. Ferguson; James D. Watson, all of Auckland, New Zealand

[73] Assignee: Biostore New Zealand, Ltd., Parnell, New Zealand

[*] Notice: This patent is subject to a terminal disclaimer.

[21] Appl. No.: 09/085,318

[22] Filed: May 26, 1998

Related U.S. Application Data

[63] Continuation-in-part of application No. 08/989,470, Dec. 12, 1997, Pat. No. 5,962,213, which is a continuation-in-part of application No. 08/842,553, Apr. 15, 1997, which is a continuation-in-part of application No. 08/722,306, Sep. 30, 1996, Pat. No. 5,827,640, which is a continuation-in-part of application No. 08/662,244, Jun. 14, 1996, Pat. No. 5,879,875.

[51] Int. Cl.⁷ ...................................................... A01N 1/02
[52] U.S. Cl. ............................ 435/1.1; 435/1.2; 435/1.3; 435/2
[58] Field of Search ............................... 435/1.1, 1.2, 1.3, 435/2

[56] References Cited

U.S. PATENT DOCUMENTS

| | | |
|---|---|---|
| 4,040,785 | 8/1977 | Kim et al. . |
| 4,380,582 | 4/1983 | Orlando et al. . |
| 4,476,221 | 10/1984 | Kane et al. . |
| 4,704,352 | 11/1987 | Heaton . |
| 4,879,283 | 11/1989 | Belzer et al. . |
| 4,897,353 | 1/1990 | Carpenter et al. . |
| 4,920,044 | 4/1990 | Bretan, Jr. . |
| 4,938,961 | 7/1990 | Collins et al. . |
| 4,980,277 | 12/1990 | Junnila . |
| 5,200,398 | 4/1993 | Strasberg et al. . |
| 5,242,792 | 9/1993 | Rudolph et al. . |
| 5,306,711 | 4/1994 | Andrews . |
| 5,328,821 | 7/1994 | Brendal . |
| 5,432,053 | 7/1995 | Berdyaev et al. ............................ 435/1 |
| 5,574,019 | 11/1996 | Segall et al. ................................ 514/23 |
| 5,580,856 | 12/1996 | Prestrelski et al. ......................... 514/21 |

FOREIGN PATENT DOCUMENTS

| | | |
|---|---|---|
| 6786681 | 11/1984 | Australia . |
| 0172716 | 8/1985 | European Pat. Off. . |
| 0259739 | 3/1988 | European Pat. Off. . |
| 0306132 | 3/1989 | European Pat. Off. . |
| 0556096 | 8/1993 | European Pat. Off. . |
| 228439 | 10/1985 | Germany . |
| 3625170 | 2/1987 | Germany . |
| 6293602 | 10/1994 | Japan . |
| 9003310 | 1/1992 | United Kingdom . |
| 9000349 | 1/1990 | WIPO . |
| 9106213 | 5/1991 | WIPO . |
| 9118504 | 12/1991 | WIPO . |
| 9203046 | 3/1992 | WIPO . |
| 9208347 | 5/1992 | WIPO . |
| 9218136 | 10/1992 | WIPO . |
| 9220300 | 11/1992 | WIPO . |
| 9300807 | 1/1993 | WIPO . |
| 9314191 | 7/1993 | WIPO . |
| 9429691 | 12/1994 | WIPO . |

OTHER PUBLICATIONS

Molinia et al., Effect of monosaccharides and disaccharides in Tris–based diluents on motility, acrosome integrity and fertility of pellet frozen ram spermatozoa., *Animal Reproduction Sci. 36*, 113–122, 1994.

Yano et al., Butyrate increases catalase activity and protects rat pulmonary artery smooth muscle cells against hyperoxia, *Biochem. and Biophys. Research Commun 164*(3), 1143–1148, 1989.

Staecker et al., Sodium butyrate preserves aspects of the differentiated phenotype of normal adult rate hepatocytes in culture, *Journal of Cellular Physiology 135*, 367–376, 1988.

Park et al., Effects of Cryoprotectants in minimizing physiochemical changes of bovine natural actomyosin during frozen storage, *J. Food Biochem 11*(2), 143–161, 1987.

Boutron et al., Reduction in Toxity for Red Blood Cells in Buffered Solutions containing high Concentrations of 2.3–Butanediol by Trehalose, Sucrose, Sorbitol or Mannitol, *Cryobiology 31*(4), 367–373, 1994.

Karow et al., Effects of Temperature, Potassium Concentration, and Sugar on Human Spermatozoa Motility: A Cell Preservation Model from Reproductive Medicine, *Cryobiology 29*, 250–254, 1992.

Newman et al., The Role of Trehalose and other Carbohydrates in Biopreservation, *Biotechnology and genetic engineering reviews 11*, 263–294, 1993.

Hogman et al., Red Cell Preservation in Protein–Poor Media, *Vox Sanguinis 41*, 274–281, 1981.

Stibenz, Preservation of Resuspended Red Cell Concentrates, Rate of Vesiculation and of Spontaneous Hemolysis, *Folia haematologica. Internationales magazin fur klinische und morphologische hamatologie 114*(4), 469–470, 1987.

(List continued on next page.)

*Primary Examiner*—Sandra Saucier
*Attorney, Agent, or Firm*—Ann W. Speckman; Janet Sleath

[57] ABSTRACT

The present invention provides solutions and methods for preserving living biological materials that enable organs, tissues and cells to be stored for extended periods of time with minimal loss of biological activity. The inventive solutions are substantially isotonic with the biological material to be preserved and are substantially free of dihydrogen phosphate, bicarbonate, nitrate, bisulfate and iodide. In one embodiment preferred for the preservation of platelets, the solutions comprise betaine, sodium chloride and sodium citrate. For the preservation of many living biological materials, the inventive solutions preferably contain a calcium salt selected from the group consisting of calcium sulfate and calcium chloride.

25 Claims, 36 Drawing Sheets

OTHER PUBLICATIONS

Shier, Studies on the Mechanisms of Mammalian Cell Killing by a Freeze–Thaw Cycle: Conditions that Prevent Cell Killing Using Nucleated Freezing, *Cryobiology 25*, 110–120, 1988.

Brearley et al., A comparative study of the cryopreservation of human erythrocytes, ghosts and liposomes, *Biochemical Society Transaction 16*, 354, 1988.

Goldstein et al., Enhanced transfection efficiency and improved cell survival after electroporation of G2/M–synchronized cells and treatment with sodium butyrate, *Nucleic acid res. 17*(10), 3959–71, 1989.

Fabre et al., Effects of different substances (sucrose, glucose, sorbitol and mannitol) on the resistance to deep freezing in liquid nitrogen of meristems from in vitro cultured carnations, *Comptes rendus de l'Acadenie des Sciences Serie III, Sciences de la vie 304*(20), 507–510, 1987.

Brass et al., Evaluation of University of Wisconsin Cold--Storage Solution in Warm Hypoxic Perfusion of Rat Liver: the Addition of Fructose Reduces Injury, *Gastroenterology 105*(5), 1455–1463, 1993.

Fremes et al., Cardiac Storage with UW Solution and Glucose, *The Annals of thoracic surgery 58*(5), 1368–1372, 1994.

Eschwege et al., Successful –4° C. Liver Preservation in Rats with University of Wisconsin Solution and 2–3–Butanediol, *Transplantation Proceedings 27*(4), 2514–2515, 1995.

Minor et al., Effects of taurine on liver preservation in UW solution with consecutive ischemic rewarming in the isolated perfused rate liver, *Transplantation international 8*, 174–179, 1995.

Ahmad et al., Deep Freezing of Buffalo Bull Semen of Nili–ravi Breed, *Indian Journal of Animal Health 22*(2), 111–114, 1983.

Shier et al., Isotonic sucrose improves cryopreservation of cultured mammalian cells, *In Vitro Cell Devel. Biol. 31*, 336–337, 1995.

Strauss et al., SAG–sucrose medium for red blood cell preservation, *Biomed. Biochem, Acta 46*, S295–299, 1987.

Clark et al. Studies on Water in Barnacle Muscle Fibres. II. Role of Ions and Organic Solutes in Swelling of Chemically–Skinned Fibres. *J. Exp. Biol.* 1981. 90:43–63.

Philippa M. Wiggins, Osmosis and Micro–osmosis, *NZ Science Review 51:*3, pp. 79–84, 1994.

Philippa M. Wiggins, Role of Water in Some Biological Processes, *Microbiological Reviews 54:*4, pp. 432–449, Dec. 1990.

Kim D. Collins et al., The Hofmeister effect and the behaviour of water at interfaces, *Quarterly Review of Biophysics 18:*4, pp. 323–422, 1985.

Leiper et al., "Adsorption of water and solute from glucose–electrolyte solutions in the human jejunum", Scand. J. Gastroenterol. 24 (9) : 1089–94 (1989).

So et al., "The effects of different buffers on glycolysis in rat liver during cold ischemic preservation", Biochem. Soc. Trans. 25 (3) : 416S (1997).

Carpenter et al., "Cryoprotection of Phosphofructokinase with Organic Solutes: Characterization of Enhanced Protection in the Presence of Divalent Cations", Archives Biochem. Biophys. 250 (2) : 505–12 (1986).

A = TMAO
B = BETAINE
C = SARCOSINE
D = GLUCOSE
E = MANNOSE
F = FRUCTOSE
G = GALACTOSE
H = RIBOSE
I = SORBITOL
J = INOSITOL
K = TAURINE

A = TMAO
B = BETAINE
C = SARCOSINE
D = GLUCOSE
E = MANNOSE
F = FRUCTOSE
G = GALACTOSE
H = RIBOSE
I = SORBITOL
J = INOSITOL
K = TAURINE
L = PBS

A = TMAO
B = BETAINE
C = SARCOSINE
D = GLUCOSE
E = MANNOSE
F = FRUCTOSE
G = GALACTOSE
H = RIBOSE
I = SORBITOL
J = INOSITOL
K = TAURINE
L = PBS

A = TMAO
B = BETAINE
C = SARCOSINE
D = GLUCOSE
E = MANNOSE
F = FRUCTOSE
G = GALACTOSE
H = RIBOSE
I = SORBITOL
J = INOSITOL
K = TAURINE
L = PBS

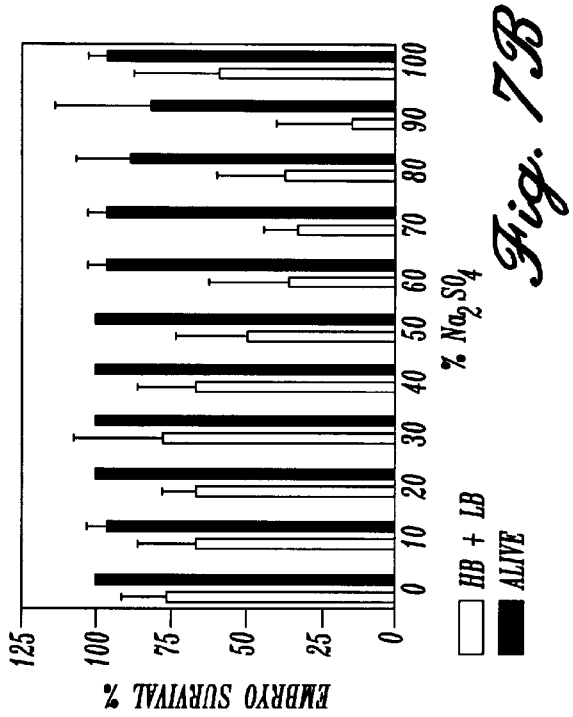
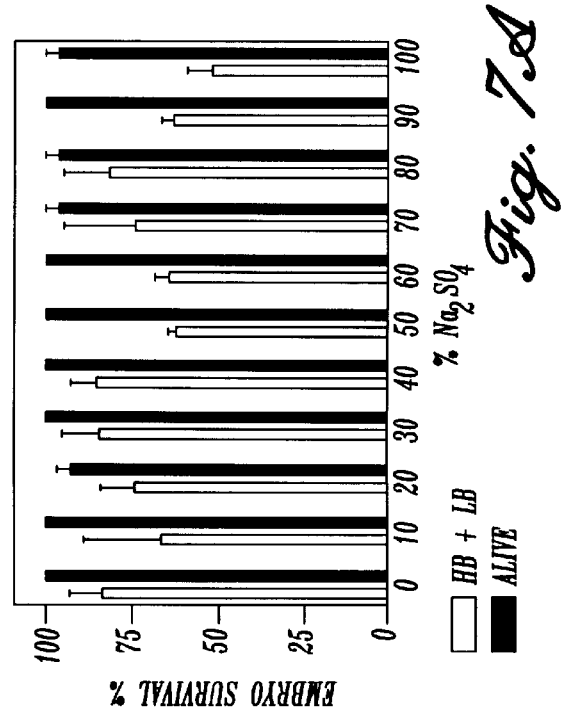
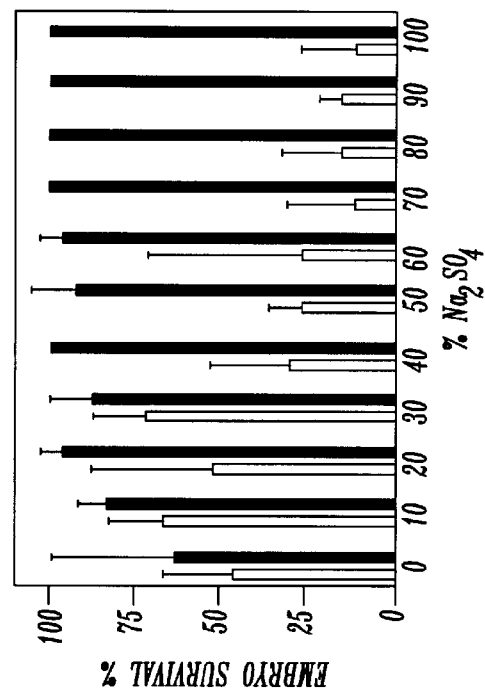

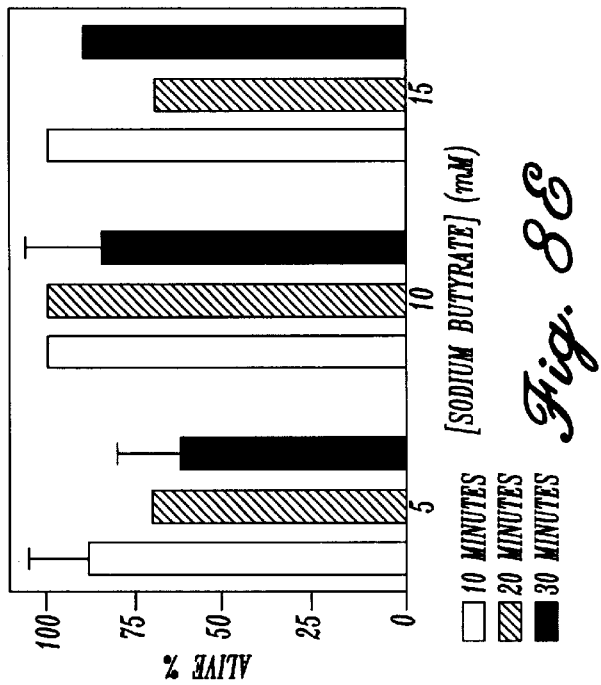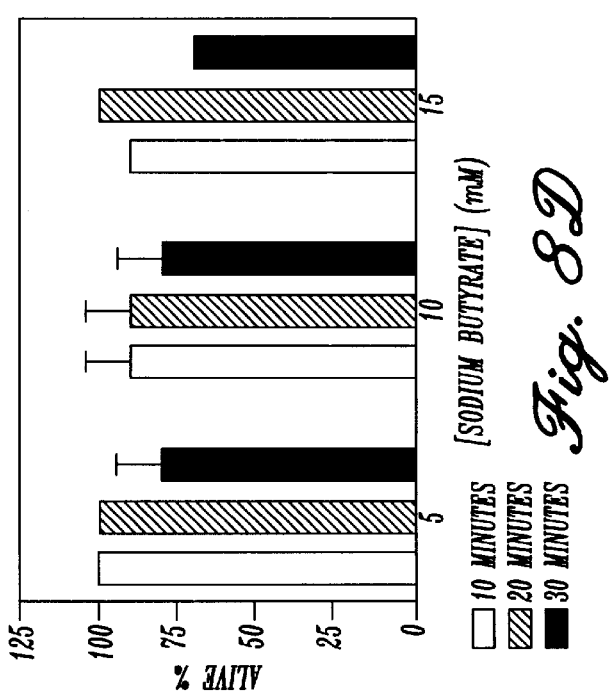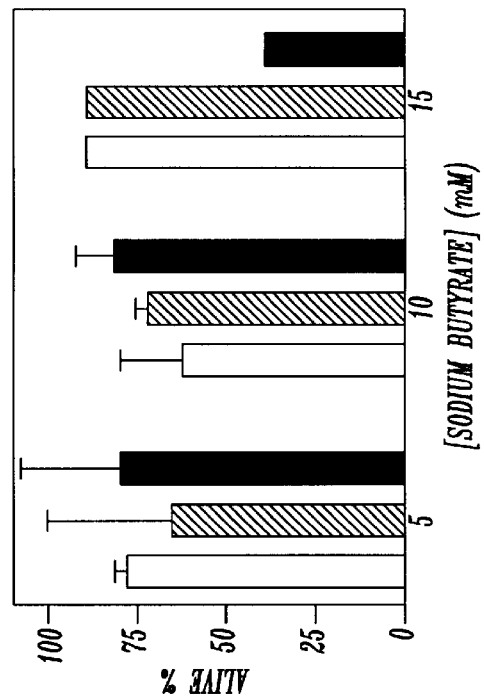

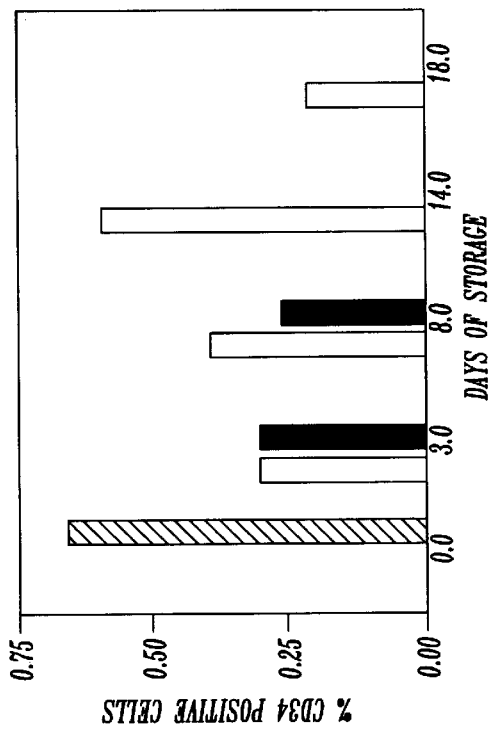
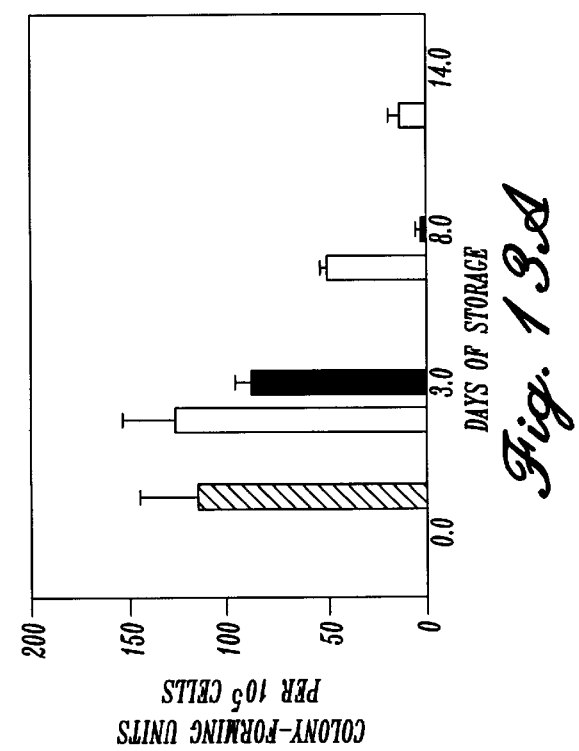
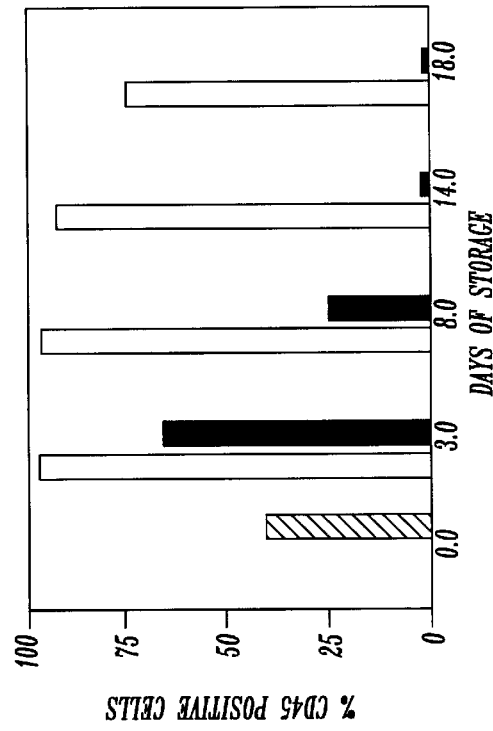
Fig. 13A
Fig. 13B
Fig. 13C
☐ RAFFINOSE/TMAO (RATIO 1.6:1); 1.75 mM CaSO₄; 0.29 OsM
■ M-2, A HERPES-BUFFERED BALANCED SALINE MEDIUM PBS = PHOSPHATE-BUFFERED SALINE
B = BETAINE
G = GALACTOSE
S = SORBITOL
M = MANNOSE
t = TREHALOSE
R = RAFFINOSE
R/T = RAFFINOSE/TMAO (RATIO 1.6:1)
R/B = RAFFINOSE/BETAINE (RATIO 1.6:1)
t/T = TREHALOSE/TMAO (RATION 1.6:1)
t/B = TREHALOSE/BETAINE (RATION 1.6:1)

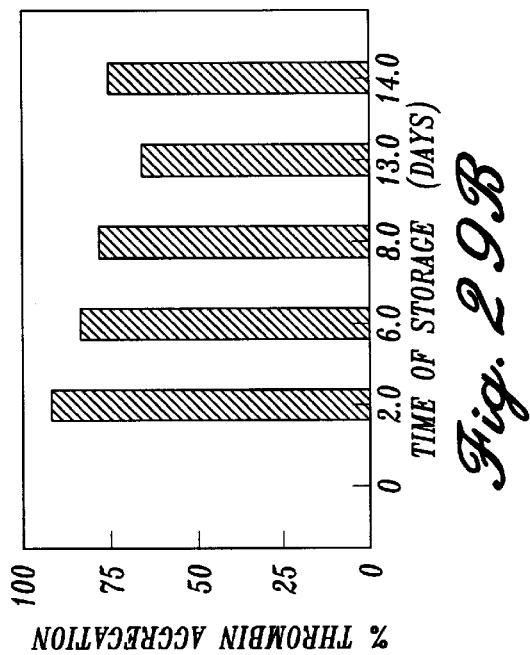
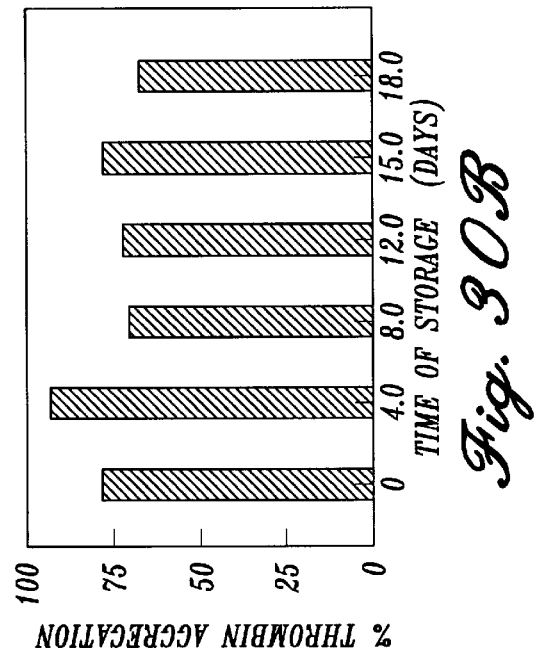
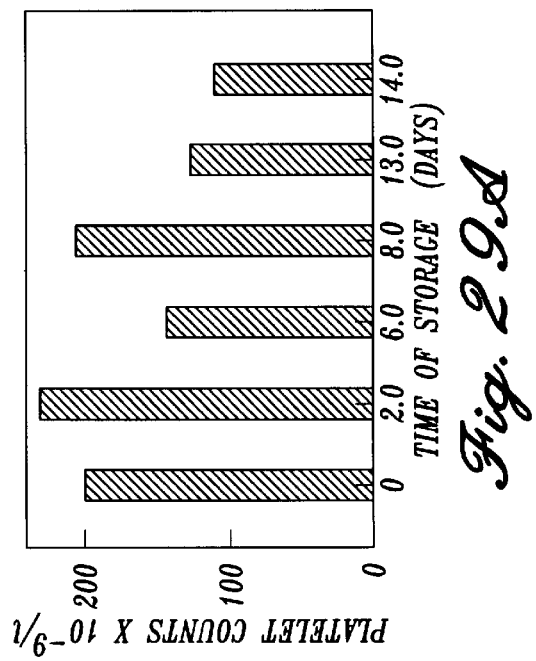
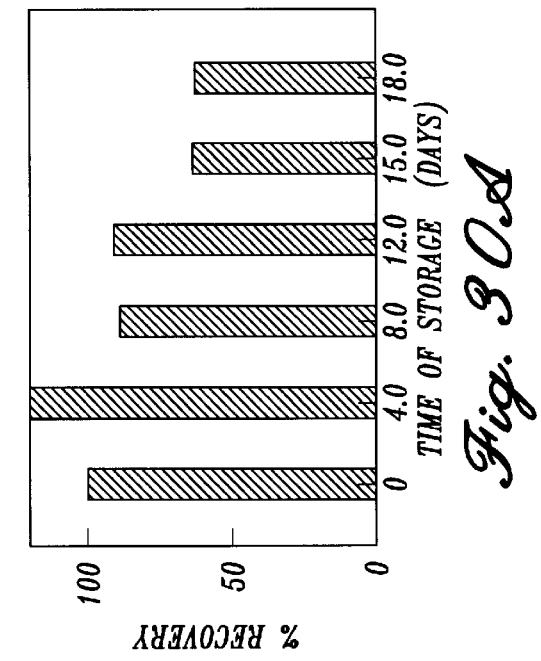

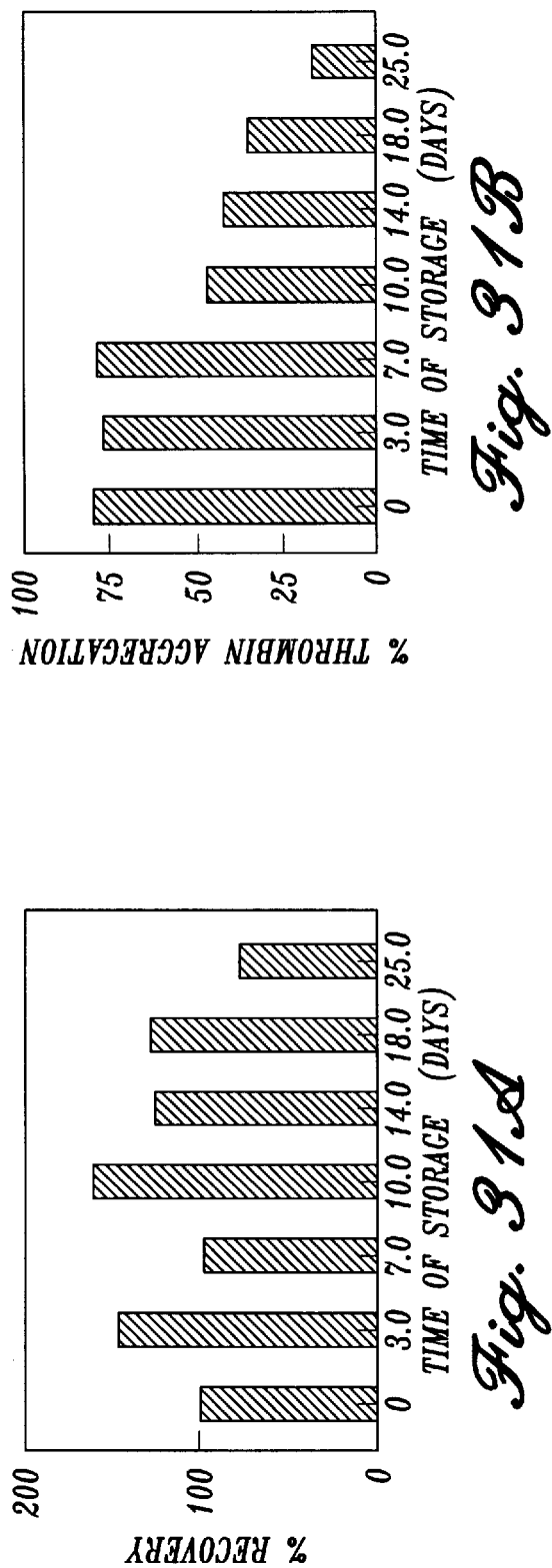
Fig. 31A
Fig. 31B
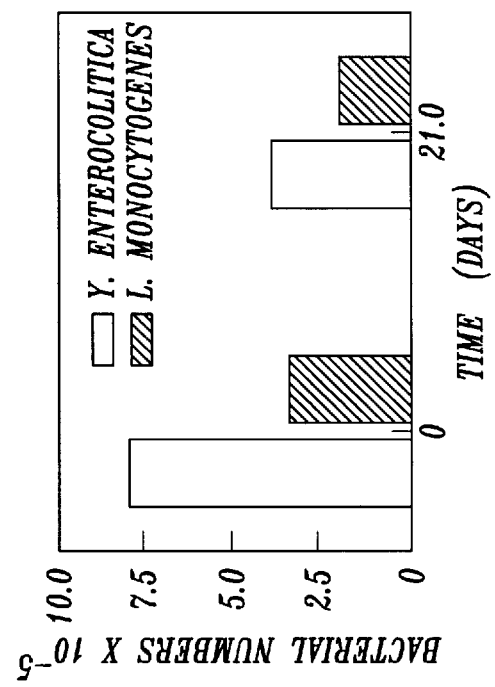
Fig. 32

COMPOSITIONS COMPRISING BETAINE, SODIUM CITRATE AND SODIUM CHLORIDE AND METHODS FOR THE PRESERVATION OF BIOLOGICAL MATERIALS

REFERENCE TO RELATED APPLICATIONS

This application is a continuation-in-part of U.S. application Ser. No. 08/989,470, filed Dec. 12, 1997, issued as U.S. Pat. No. 5,962,213 which is a continuation-in-part of U.S. application Ser. No. 08/842,553, filed Apr. 15, 1997, which is a continuation-in-part of U.S. application Ser. No. 08/722,306, filed Sep. 30, 1996, issued as U.S. Pat. No. 5,827,640 which is a continuation-in-part of U.S. application Ser. No. 08/662,244 filed Jun. 14, 1996 issued as U.S. Pat. No. 5,879,875.

TECHNICAL FIELD OF THE INVENTION

This invention relates to the field of preservation of biological materials and, more particularly, to compositions and methods for the preservation of living organs, tissues and cells from mammals, marine organisms and plants.

BACKGROUND OF THE INVENTION

Methods for the preservation of biological materials are employed in many clinical and veterinary applications wherein living material, including organs, tissues and cells, is harvested and stored in vitro for some period of time before use. Examples of such applications include organ storage and transplants, autologous and allogeneic bone marrow transplants, whole blood transplants, platelet transplants, embryo transfer, artificial insemination, in vitro fertilization, skin grafting and storage of tissue biopsies for diagnostic purposes. Preservation techniques are also important in the storage of cell lines for experimental use in hospital, industrial, university and other research laboratories.

Methods currently employed for the preservation of cellular biological materials include immersion in saline-based media; storage at temperatures slightly above freezing; storage at temperatures of about −80° C.; and storage in liquid nitrogen at temperatures of about −196° C. The goal of all these techniques is to store living biological materials for an extended period of time with minimal loss of normal biological structure and function.

Storage of organs, such as heart and kidneys, at temperatures below 0° C. frequently results in the loss of many cells with a corresponding reduction in viability of the organ. Such complex biological materials are therefore typically stored in aqueous, saline-based media at temperatures above freezing, typically around 4° C. Saline-based media typically consist of isotonic saline (sodium chloride 0.154 M) which has been modified by the addition of low concentrations of various inorganic ions, such as sodium, potassium, calcium, magnesium, chloride, phosphate and bicarbonate, to mimic the extracellular environment. Small amounts of compounds such as glucose, lactose, amino acids and vitamins are often added as metabolites. All saline-based media used for preservation of biological materials have high electrical conductivity. Examples of media currently employed for the preservation of biological materials include phosphate-buffered saline (PBS), M-2 (a Hepes buffered murine culture medium), Ringer's solution and Krebs bicarbonate-buffered medium.

The viability of biological materials stored in saline-based media gradually decreases over time. Loss of viability is believed to be due to the build-up of toxic wastes, and loss of metabolites and other supporting compounds caused by continued metabolic activity. Using conventional saline-based media, living tissues can only be successfully preserved for relatively short periods of time. Examination of the microstructure of organs stored towards the upper limit of time shows degeneration, such as of mitochondria in heart muscle, and the performance of the organ once replaced is measurably compromised. For example, a human heart can only be stored in cold ionic solutions for about 5 hours following removal from a donor, thereby severely limiting the distance over which the heart can be transported.

When employing freezing techniques to preserve biological materials, high concentrations (approximately 10% by volume) of cryoprotectants, such as glycerol, dimethylsulfoxide (DMSO), glycols or propanediol, are often introduced to the material prior to freezing in order to limit the amount of damage caused to cells by the formation of ice crystals during freezing. The choice and concentration of cryoprotectant, time-course for the addition of cryoprotectant and temperature at which the cryoprotectant is introduced all play an important role in the success of the preservation procedure. Furthermore, in order to reduce the loss of cells, it is critical that such variables as the rate and time-course of freezing, rate and time-course of thawing and further warming to room or body temperature, and replacement of cryoprotectant solution in the tissue mass with a physiological saline solution be carefully controlled. The large number of handling steps required in freezing techniques increases the loss of cells. The freezing techniques currently employed in the preservation of biological materials are both technically demanding and time consuming. Other disadvantages of preserving biological materials by freezing include: reduction of cell viability; potential toxic effects of the cryoprotectant to the patient upon re-infusion; and the high costs of processing and storage.

As an example, cryopreservation, generally including the addition of DMSO as a cryoprotectant, is presently used to store bone marrow harvested for use in transplantation procedures following, for example, high dose chemotherapy or radiotherapy. In autologous transplants the bone marrow must be preserved for prolonged periods, ranging from weeks to months. However, this technique results in significant reduction of stem cell recovery, to levels as low as 50% or less. An additional disadvantage of this technique is that significant damage to various mature cells can occur, thereby requiring further processing to remove these cells prior to freezing. Finally, the use of DMSO results in moderate to severe toxicity to the patient on re-infusion of the preserved bone marrow.

There thus remains a need in the art for improved methods for the preservation of living biological materials.

SUMMARY

The present invention provides compositions and methods for preserving living biological materials that enable materials including organs, tissues and cells to be stored for extended periods of time with minimal loss of biological activity.

In one aspect, the present invention provides solutions for preserving the viability of living biological materials, comprising a first neutral solute with no net charge, having a molecular weight of at least about 335 and a solubility in water of at least about 0.3 M; and a second neutral solute having a molecular weight of less than about 200, the second solute additionally having both hydrophilic and hydrophobic moieties.

In a preferred embodiment, the first neutral solute is either a disaccharide or a trisaccharide, preferably selected from the group consisting of raffinose, trehalose, sucrose, lactose and analogs thereof. The analogs may be either naturally occurring or synthetic. The second neutral solute is preferably selected from the group consisting of trimethyl amino oxide (TMAO), betaine, taurine, sarcosine, glucose, mannose, fructose, ribose, galactose, sorbitol, mannitol, inositol and analogs thereof. Most preferably, the first neutral solute is selected from the group consisting of raffinose and trehalose, and the second neutral solute is selected from the group consisting of trimethyl amine oxide (TMAO) and betaine.

Preservation solutions of the present invention may also include one or more ions. In one embodiment, the preservation solutions employed in the inventive methods also comprise sodium sulfate and calcium, the calcium preferably being present as calcium sulfate or calcium chloride at a concentration of more than about 1.5 mM or less than about 2.0 mM. Preferably the calcium chloride is present at a concentration of about 1.5 mM to about 2.0 mM, most preferably about 1.75 mM.

While the preferred solution for the preservation of a biological material will depend upon the specific biological material to be preserved, in one aspect it has been found that solutions comprising either raffinose and TMAO, raffinose and betaine, or trehalose and TMAO are particularly efficacious in the preservation of many biological materials. In one embodiment, the inventive solutions comprise raffinose and either TMAO or betaine in a molar ratio of less than about 2.0:1 or more than about 1.1:1. Preferably the preservative solutions of this aspect comprise raffinose and either TMAO or betaine in a molar ratio between about 1.1:1 to about 2.0:1, more preferably about 1.4:1 to about 1.8:1, and most preferably about 1.6:1. Preferably, the solutions of this aspect of the present invention comprise TMAO or betaine at a concentration of about 70–75 mM, most preferably about 72 mM; raffinose at a concentration of about 120–130 mM, most preferably about 126 mM; sodium sulphate at a concentration of about 35–45 mM, most preferably about 39 mM; and calcium sulphate at a concentration of about 1.5–2.0 mM, most preferably about 1.75 mM.

In another embodiment, the inventive preservation solutions comprise a first neutral solute and a second neutral solute as defined above, preferably raffinose and TMAO, in combination with an equiosmolar amount of sodium citrate and with calcium chloride, the calcium chloride preferably being present at a concentration of more than about 1.5 mM or less than 2.0 mM, more preferably at a concentration from about 1.5 mM to about 2.0 mM, and most preferably about 1.75 mM. Preferably, the solution comprises more than about 10% and less than about 30% sodium citrate, more preferably between about 10% and about 30% sodium citrate.

In another aspect, the present invention provides solutions for preserving the viability of living biological materials, comprising TMAO, sodium chloride and calcium chloride. In one embodiment, the preservation solutions comprise TMAO at a concentration of more than about 150 mM or less than about 230 mM, more preferably at a concentration of between about 150 mM and about 230 mM and most preferably at a concentration of between about 160 mM and about 215 mM; sodium chloride at a concentration of more than about 30 mM or less than about 60 mM, more preferably between about 30 mM and about 60 mM and most preferably at a concentration of about 46.8 mM; and calcium chloride at a concentration of more than about 1.5 mM or less than about 2.0 mM, more preferably at a concentration between about 1.5 mM and about 2.0 mM, and most preferably at a concentration of about 1.75 mM.

In a further aspect, the present invention provides solutions for the preservation of living biological materials that comprise either betaine or trimethyl amine oxide, sodium citrate and sodium chloride, with the betaine or TMAO preferably being present at a concentration greater than about 150 mM or less than 220 mM, more preferably between about 150 mM and about 220 mM, and most preferably at a concentration of about 184 mM for TMAO or 187 mM for betaine; the sodium citrate preferably being present at a concentration greater than about 1.5 mM or less than about 2.5 mM, more preferably between about 1.5 mM and about 2.5 mM, and most preferably at a concentration of about 1.96 mM; and the sodium chloride preferably being present at a concentration greater than about 35 mM or less than about 55 mM, more preferably between about 35 mM and about 55 mM, and most preferably at a concentration of about 45.8 mM. The solutions of this aspect of the present invention have been found to be particularly efficacious in the preservation of platelets.

In yet another aspect, a method for the treatment of leukemia is provided, the method comprising removing bone marrow from a patient, contacting the bone marrow with a preservation composition or solution of the present invention for a period of at least about 3 days at a temperature of less than about 0° C., more preferably between about –4° C. and about –80° C., and most preferably at a temperature of about –80° C., in order to purge the bone marrow of leukemic cells, and returning the purged bone marrow to the patient.

As detailed below, it has been found that the solutions and methods of the present invention can be employed to maintain the viability of living biological materials, including cells, tissues and organs, for longer periods of time than are generally possible with conventional preservation methods, thereby providing improved storage and transport times for biological materials for use in applications such as organ transplants and bone marrow transplants.

The preservation methods of the present invention are less complex than many of the methods typically employed for the preservation of biological materials, thereby reducing costs and increasing the ease of use and availability of preservation procedures. Furthermore, the inventive compositions are of low toxicity, resulting in fewer negative side effects when biological materials, such as transplant organs, are returned to a patient.

The above-mentioned and additional features of the present invention and the manner of obtaining them will become apparent, and the invention will be best understood by reference to the following more detailed description, read in conjunction with the accompanying drawings.

BRIEF DESCRIPTION OF THE DRAWINGS

FIGS. 7A, B and C show the survival of mouse embryos following storage for 1, 2 and 3 days, respectively, at 4° C. in mixtures of raffinose/TMAO and $Na_2SO_4$, with 1.75 mM $CaSO_4$.

FIGS. 13A, B and C show the percentage of colony forming units, CD34- and CD45-positive cells, respectively, in bone marrow from patient 2 following storage in either raffinose/TMAO with 1.75 mM $CaSO_4$ or in M-2 at 4° C.

FIGS. 29A and B show platelet counts and their percentage thrombin-activated aggregation, respectively, following preparation in tubes and storage at 4° C. in Solution 70/30C2 in glass tubes coated with dichlorodimethyl silane.

FIGS. 30A and B show percentage recovery of platelets and their percentage thrombin-activated aggregation, respectively, following preparation in bags and storage at 4° C. in Solution 70/30C2 in a single glass bottle coated with dichlorodimethyl silane.

FIGS. 31A and B show percentage recovery of platelets and their percentage thrombin-activated aggregation, respectively, following preparation in bags and storage at 4° C. in the same bags containing Solution 70/30C2.

FIG. 32 shows that two micro-organisms, both of which grow at 4° C. in nutrient broth, failed to grow during storage of platelets in Solution 70/30C2 at 4° C.

DETAILED DESCRIPTION

Figure 1A:
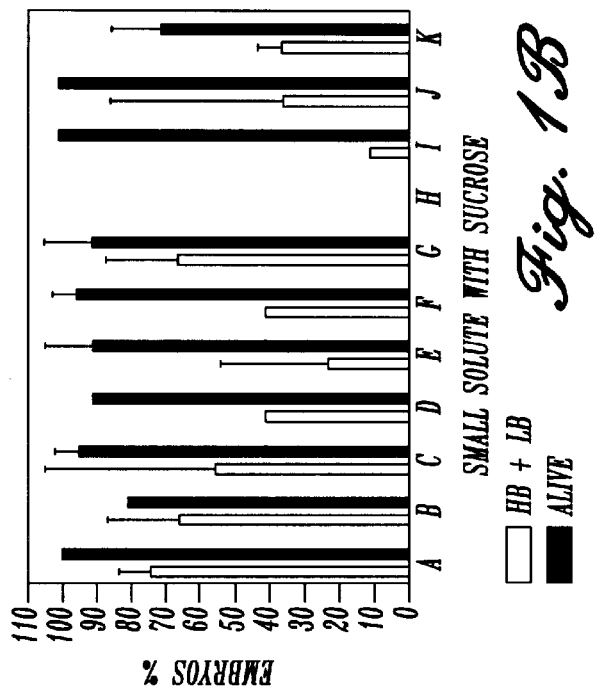
FIGS. 1A, B and C illustrate the survival of mouse embryos following 1, 2 and 3 days of storage, respectively, at 4° C. in an aqueous solution of sucrose and various Class II solutes, together with 1.75 mM $CaSO_4$.
Figure 1B:
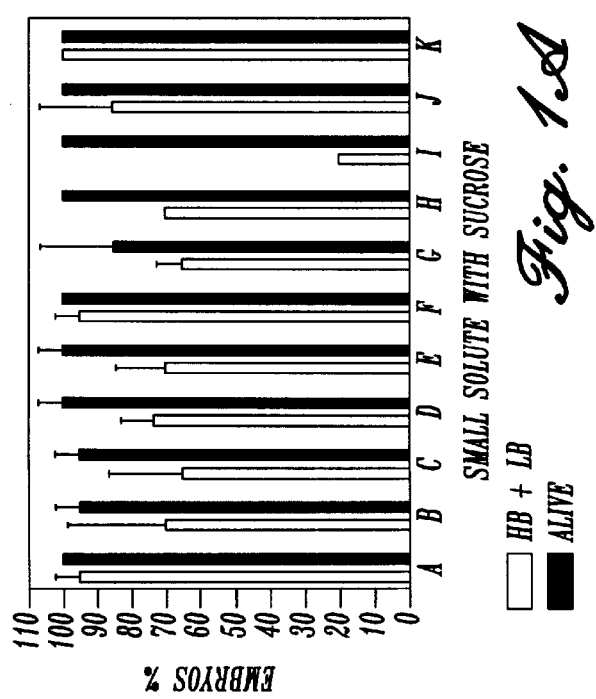
Figure 1C:
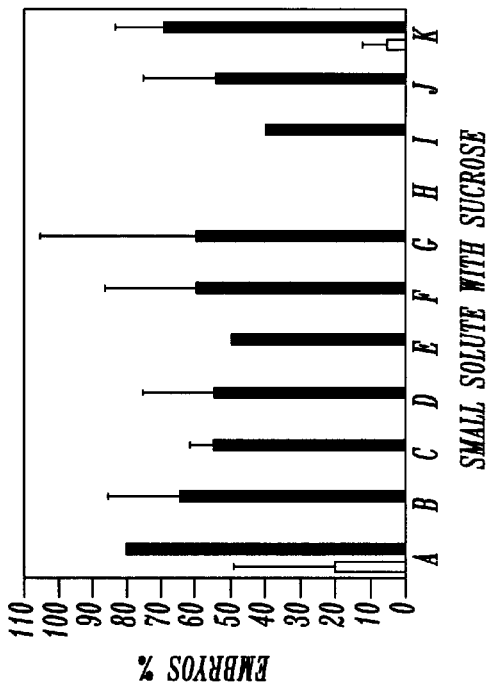

The solutions and methods of the present invention may be used in the preservation of living biological materials including mammalian, plant and marine cells, cell lines, tissues and organs. When a living biological material is preserved, its viability is maintained in vitro for an extended period of time, such that the material resumes its normal biological activity on being removed from storage. During storage the biological material is thus maintained in a reversible state of dormancy, with metabolic activity being substantially lower than normal. For example, hearts are observed to stop beating during storage. Examples of mammalian biological materials which may be preserved using the present invention include, but are not limited to, organs, such as heart, kidneys, lungs and livers; cells and tissues such as haematopoietic stem cells, bone marrow, embryos, platelets, osteoblasts, spermatozoa, granulocytes, red blood cells, dendritic cells, oocytes; and various animal cell lines established in tissue culture. In addition to the preservation of human biological materials, the inventive solutions and methods may also be employed in veterinary applications, and for preservation of plant and marine tissues.

The preservative solutions of the present invention may be in either a ready-to-use form or may be provided in a concentrated form, such as a solid, including for example, powder or tablets, which is reconstituted in water prior to use. The inventive solutions may also be provided in a concentrated liquid form for dilution by the user. As with conventional preservative solutions, the inventive solutions are sterile.

The solutions of the present invention are substantially isotonic with the biological material to be preserved. Cells in an isotonic solution neither shrink nor swell substantially. Preferably, the preservative solutions of the present invention have an osmolality substantially equal to that of the biological material to be preserved. However, this is not a requirement of all the inventive solutions, since some solutions may include one or more components which raise the osmolality of the solution but are able to cross semipermeable membranes freely, thus raising the osmotic pressure equally on both sides of the cell membrane.

As detailed below, it has been determined that an osmolality of between about 280 mOsM and about 320 mOsM is preferable for solutions for the preservation of mammalian biological materials. Osmolalities of between about 900 mOsM to about 1000 mOsM and between about 70 mOsM to about 80 mOsM are preferred for the preservation of marine and plant biological materials, respectively.

The inventive solutions may include oxyanions, such as dihydrogen phosphate, bicarbonate, nitrate, nitrite, bisulfate, chlorate, perchlorate, bromate, permanganate, iodate, periodate, trichloroacetate, bromoacetate and dihydrogen phosphite, at concentrations less than about $10^{-5}$M. However, it has been observed that the presence of univalent oxyanions in preservation solutions may increase the level of metabolic activity during storage. For example, in preservation solutions comprising $HSO_4$, a rat heart was observed to beat slowly and feebly, whereas in preservation solutions that did not comprise univalent oxyanions, no beating was observed to occur. For most applications, preservative solutions of the present invention preferably reversibly depress the level of metabolic activity during storage, and preferably are substantially free of univalent oxyanions.

Similarly, it has been found that the presence of iodide ions reduces the effectiveness of the preservative solutions and thus the inventive solutions are preferably substantially free of iodide ions. As used herein the term "substantially free" means that the concentration of ions is below that required to raise the metabolic activity of the material to be preserved during storage.

In one aspect, the inventive solutions comprise a first neutral solute having a molecular weight of at least about 335 and a solubility in water of at least about 0.3 M (hereinafter referred to as Class I solutes), and a second neutral solute having a molecular weight of less than about 200 (hereinafter referred to as Class II solutes), the second neutral solute additionally having both hydrophilic and hydrophobic moieties. Class I solutes are generally too large to penetrate cell membranes and act primarily to raise the osmolality of the inventive solutions. Preferably, Class I solutes are disaccharides or trisaccharides. Examples of such solutes include raffinose, trehalose, sucrose, lactose and synthetic or naturally occurring analogs thereof, with raffinose and trehalose being preferred Class I solutes.

Class II solutes generally do not passively cross cell membranes, but may be actively taken up by cells in response to an osmotic insult. They are used by many cells as intracellular osmolytes. Examples of such solutes include TMAO, betaine, taurine, sarcosine, glucose, mannose, fructose, ribose, galactose, sorbitol, mannitol and inositol and synthetic or naturally occurring analogs thereof, with TMAO and betaine being preferred Class II solutes. In one embodiment, the inventive solutions comprise either (a) raffinose and TMAO, preferably in a molar ratio greater than about 1.1:1 or less than about 2.0:1, more preferably in a molar ratio of between about 1.4:1 to about 1.8:1 and most preferably in a molar ratio of about 1.6:1; (b) trehalose and TMAO, preferably in a molar ratio greater than about 1.1:1 or less than about 1.4:1, more preferably in a molar ratio of between about 1.1:1 and about 1.4:1, and most preferably in a molar ratio of about 1.3: 1, (c) raffinose and betaine, preferably in a molar ratio of less than about 1.7:1 or greater than about 1.3:1, more preferably in a molar ratio of between about 1.3:1 and about 1.7: 1, and most preferably in a molar ratio of between about 1.4:1 and about 1.6: 1; or (d) trehalose and betaine, preferably in a molar ratio of less than about 1.7:1 or greater than about 1.3:1, more preferably in a molar ratio of between about 1.3:1 and about 1.7:1, and most preferably in a molar ratio of between about 1.4:1 and about 1.6:1.

The inventive solutions may additionally contain one or more ions but, as noted above, are substantially free of univalent oxyanions and iodide. A calcium salt, such as $CaSO_4$ or $CaCl_2$, is used at concentrations below about 2 mM in preservation solutions for many applications. Other ionic species may be selected according to their ability to suppress metabolism during storage.

As detailed below, it has been determined that, with the exception of platelets, effective storage times for biological materials increase with the addition of calcium to the preservative compositions. This may be due to the ability of calcium to stabilize phospholipid bilayers found in cell membranes and to stabilize intercellular adhesion. Preferably the calcium is present as calcium sulfate or calcium chloride, and is present at a concentration greater than about 1.5 mM or less than about 2.0 mM, more preferably at a concentration of between about 1.5 mM and about 2.0 mM, and most preferably about 1.75 mM. The addition of either sodium sulfate or sodium citrate also increases effective storage times for many biological materials.

A solution comprising the following components has been found to be particularly effective in preserving many biological materials: between about 60% and about 80% by volume, preferably about 70%, of a solution of raffinose and TMAO; between about 40% and about 20% by volume, preferably about 30% of a solution of sodium sulfate; and about 1.75 mM calcium sulfate, wherein the raffinose and TMAO are present in a ratio of about 1.6:1, and wherein both the solution of raffinose and TMAO and the solution of sodium sulfate are isotonic with the material to be preserved. The concentrations of solutes in this embodiment of the present invention are preferably as follows: TMAO about 70–75 mM, most preferably about 72 mM; raffinose about 120–130 mM, most preferably about 126 mM; sodium sulphate about 35–45 mM, most preferably about 39 mM; and calcium sulphate about 1.5–2.0 mM, most preferably about 1.75 mM.

The preservative solutions of the present invention may be conveniently prepared by first making individual solutions of the separate components, with each individual solution being of the desired osmolality. The individual solutions are then mixed in the desired proportions to provide the inventive solutions. For example, to prepare a preferred embodiment of the inventive solutions for the preservation of mammalian biological materials (referred to as Solution 70/30), solutions of TMAO, raffinose, sodium sulfate and calcium chloride having the following concentrations are first prepared:

| | |
|---|---|
| TMAO dihydrate | 29.7 g/l |
| raffinose | 147.1 g/l |
| anhydrous sodium sulfate | 18.6 g/l |
| calcium chloride dihydrate | 17.1 g/l |

Each of these solutions has an osmolality of 290 mOsM. These solutions are then mixed in the following amounts to give the following final concentrations:

| | Volume (ml) | final concentration (g/l) | final concentration (mM) |
|---|---|---|---|
| TMAO | 134.5 | 7.88 | 71 |
| raffinose | 215.5 | 62.5 | 124 |
| sodium sulphate | 150 | 5.5 | 38.7 |
| calcium chloride | 7 | 0.24 | 1.6 |

This gives a proportion of raffinose to TMAO to sodium sulfate of 1:0.62:0.70. For use with non-mammalian biological materials, the solutions may be made up to an osmolality between about 900 mOsM and about 1000 mOsM for marine materials, and between about 70 mOsM and about 80 mOsM for plant materials, and mixed in the same ratios.

A composition comprising raffinose, TMAO, sodium citrate and calcium chloride has also been found to be highly effective in the preservation of biological materials. In one embodiment, such solutions comprise, in an amount that is equiosmolar to the material to be preserved, raffinose and TMAO in a molar ratio greater than about 1.1:1 or less than about 2.0:1, preferably between about 1.1:1 and about 2.0:1, more preferably between about 1.4:1 and about 1.8:1, and most preferably of about 1.6:1; an equiosmolar amount again, to the material to be preserved, of sodium citrate; and greater than about 1.5 mM or less than about 2.0 mM, preferably between about 1.5 mM and about 2.0 mM, calcium chloride. Preferably, the calcium chloride is present at a concentration of about 1.75 mM, with the sodium citrate preferably being present in an amount greater than about 10% or less than about 30% by volume of a solution equiosmolar to the material to be preserved, more preferably between about 10% and about 30%. Preferably, the sodium citrate is present at a concentration greater than about 5 mM or less than about 20 mM, more preferably, between about 10 mM and about 20 mM.

In one embodiment, such solutions are made from stock solutions of TMAO, raffinose, sodium citrate and calcium chloride, each of which is equiosmolar to the material to be preserved. For example, for mammalian tissues of osmolality 0.29 OsM the stock solutions contain:

| | |
|---|---|
| TMAO dihydrate | 29.7 g/l |
| raffinose | 147.1 g/l |
| sodium citrate dihydrate | 29.0 g/l |
| calcium chloride dihydrate | 17.1 g/l |

The volumes of these solutions used and the final concentrations of the solutes are:

| | Volume (ml) | final concentration (g/l) | final concentration (mM) |
|---|---|---|---|
| TMAO | 173–134.6 | 10.2–7.9 | 91.9–71.7 |
| raffinose | 276–215 | 80.1–63.3 | 159–125 |
| sodium citrate | 50–150 | 2.9–8.7 | 9.9–17 |
| calcium chloride | 7 | 0.25 | 1.7 |

In another aspect, the inventive compositions comprise a Class II solute in combination with sodium chloride and a calcium salt, preferably calcium chloride. In one embodiment, such compositions comprise equiosmolar to the material to be preserved sodium chloride and TMAO, together with calcium chloride at a concentration greater than about 1.5 mM or less than about 2.0 mM, more preferably between about 1.5 mM and about 2.0 mM, and most preferably about 1.75 mM. Preferably the solution comprises TMAO in amount of more than about 60% or less than about 80% by volume of a solution having the same osmolality as the material to be preserved, more preferably between about 60% and about 80% and most preferably about 70%. The sodium chloride is preferably present in an amount less than about 40% or greater than about 5% by volume or a solution having the same osmolality as the material to be preserved, more preferably in an amount between about 40% and about 20%, and most preferably at an amount of about 30%. The sodium chloride is preferably present at a concentration between about 30 mM and about 65 mM, more preferably at a concentration of between about 40 mM and about 50 mM, and most preferably at a concentration of about 46.8 mM. The concentration of sodium chloride in the inventive compositions is therefore significantly less than that in conventional saline-based media, which typically comprise 145 mM sodium chloride.

| TMAO dihydrate | 29.7 g/l |
| --- | --- |
| sodium chloride | 9.08 g/l |
| calcium chloride dihydrate | 17.1 g/l |

The volumes of these solutions used and the final concentrations of the solutes are:

|  | Volume (ml) | final concentration (g/l) | final concentration (mM) |
| --- | --- | --- | --- |
| TMAO | 300–400 | 7.8–23.8 | 161–214 |
| sodium chloride | 200–100 | 3.6–1.82 | 62–31 |
| calcium chloride | 7 | .25 | 1.7 |

In yet another aspect, the present invention provides solutions for the preservation of living biological materials comprising a Class II solute, preferably TMAO or betaine, in combination with sodium citrate and sodium chloride. In one embodiment, such solutions comprise TMAO preferably at a concentration greater than about 150 mM or less than 220 mM, more preferably between about 150 mM and about 220 mM, and most preferably at a concentration of about 184 mM; sodium citrate preferably at a concentration greater than about 1.5 mM or less than about 2.5 mM, more preferably between about 1.5 mM and about 2.5 mM and most preferably at a concentration of about 1.96 mM; and sodium chloride preferably at a concentration greater than about 35 mM or less than about 55 mM, more preferably between about 35 mM and about 55 mM, and most preferably at a concentration of about 45.8 mM. In another embodiment, such solutions comprise betaine, preferably at a concentration greater than about 150 mM or less than 220 mM, more preferably between about 150 mM and about 220 mM, and most preferably at a concentration of about 187 mM; sodium citrate preferably at a concentration greater than about 1.5 mM or less than about 2.5 mM, more preferably between about 1.5 mM and about 2.5 mM and most preferably at a concentration of about 1.96 mM; and sodium chloride preferably at a concentration greater than about 35 mM or less than about 55 mM, more preferably between about 35 mM and about 55 mM, and most preferably at a concentration of about 45.8 mM. As discussed in detail below, it has been found that these solutions are particularly effective in the preservation of platelets.

Other components which may be included in the inventive compositions include antibiotics for the control of microorganisms, and proteins, such as bovine serum albumin, for inhibiting the attachment of the biological material, such as embryos, to surfaces. For certain applications, such as storage of hearts, the preservative solution may be saturated with oxygen before use. It has been found that the addition of buffers to the inventive preservative compositions is generally not necessary. Indeed, as noted above, the addition of univalent oxyanions, which are found in many conventional buffers, reduces the effectiveness of the preservative compositions. In preferred embodiments, the inventive compositions are therefore unbuffered.

Unlike many compositions typically used for the preservation of biological materials, the inventive compositions do not require conventional cryoprotectants, indeed the absence of conventional cryoprotectants at concentrations greater than 5% is preferred, due to their often toxic side effects. As used herein, the term "conventional cryoprotectants" refers to two types of compounds. The first includes DMSO, glycerol, ethanol, methanol and propane-diol, which have high solubilities in water and diffuse passively across cell membranes. These compounds are used at high concentrations in conventional saline media and reach similarly high concentrations inside the cells to be frozen. They are believed to act by lowering the freezing point of water. The second type of cryoprotectant consists of water-soluble polymers which cannot cross cell membranes. Examples of cryoprotectants of this type include polyethylene glycol (mw 8,000 or 20,000), human serum albumin, polyvinyl pyrrolidone (mw 30,000), dextran (mw 10,000–500,000), Ficoll (mw 70,000) and hydroxyethyl starch. Such compounds probably protect from freezing damage by inducing amorphous rather than crystalline ice.

While not wishing to be bound by theory, the inventors believe that the preservative solutions of the present invention isolate cells from external stimulatory signals carried through the cell membrane by preventing the opening of ion channels, thereby maintaining the cells in a state of dormancy.

Biological materials to be preserved are harvested using standard techniques and contacted, preferably immersed, in an aqueous preservative solution of the present invention. The biological material may be rinsed with the preservative solution prior to immersion, if desired. While the biological materials may be stored at temperatures below freezing, including temperatures as low as about –196° C., materials may be conveniently stored at temperatures of about 4° C. After storage, the preservative solution may be removed from the material and replaced with a standard saline-based medium or the stored material may be used directly in its preservative solution. When the biological material is stored at temperatures below freezing, an effective concentration of a cryoprotectant may be added to the preservative solution, as employed in techniques well known to those of skill in the art, although, as discussed above, the absence of conventional cryoprotectants at concentrations greater than about 5% is generally preferred. The inventive solutions may thus be used for either long term or short term storage of living biological materials.

As discussed in detail below, it has been found that biological materials may be effectively stored by immersing the material in an inventive preservative solution at room temperature and then immediately placing the material at a temperature below freezing, such as plunging the material into liquid nitrogen at –196° C. or placing it in a freezer at –140° C. After storage, the material is rapidly returned to room temperature by, for example, thawing in a 37° C. water bath. This method obviates the need for the slow, controlled freezing and rewarming used in conventional cryopreservation techniques, resulting in reduced costs and time requirements.

As detailed below in Example 2, storage times for some biological materials, such as embryos, may be increased by pretreatment with either a Class II solute or sodium butyrate.

The word "about," when used in this application with reference to temperature (° C.), contemplates a variance of up to 20° from the stated temperature. The word "about," when used in this application with reference to molecular weight, contemplates a variance of up to 10% from the stated molecular weight. The word "about," when used with reference to the solubility of a solute or molarity of a solution, contemplates a variance of up to 5% from the stated molarity. The word "about," when used with reference to a ratio, contemplates a variance of up to 0.2 on either side of the ratio. The word "about," when used with reference to a percentage solution composition, contemplates a variance of up to 10% from the stated percentage. The word "about," when used with reference to the osmolality of a solution, contemplates a variance of up to 10% from the stated osmolality.

The following examples are offered by way of illustration and not by way of limitation.

EXAMPLE 1

The efficacy of the solutions of the present invention in the preservation of mouse embryos was tested as described below. As embryos consist of rapidly dividing cells, they are difficult to arrest, and therefore provide a sensitive test of storage solutions. Embryos also have the advantage that survival in storage can be assessed after 1–5 days by their ability to hatch in subsequent culture.

Figure 2A:
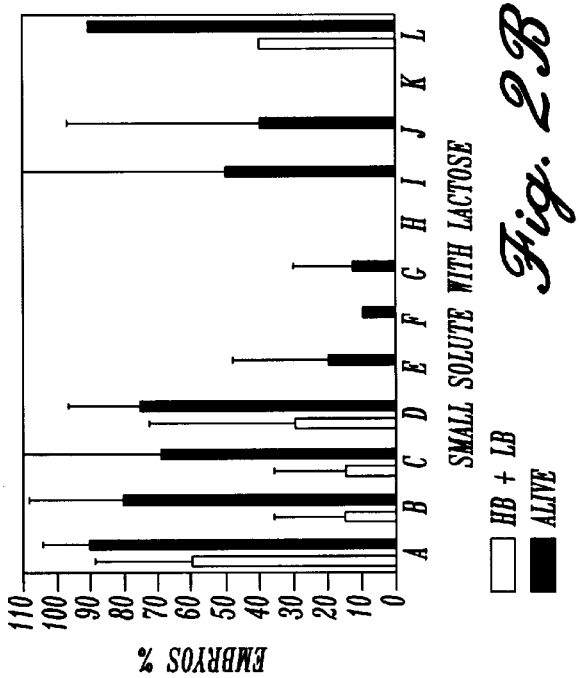
FIGS. 2A, B and C illustrate the survival of mouse embryos following 1, 2 and 3 days of storage, respectively, at 4° C. in an aqueous solution of lactose and various Class II solutes, together with 1.75 mM $CaSO_4$.
Figure 2B:
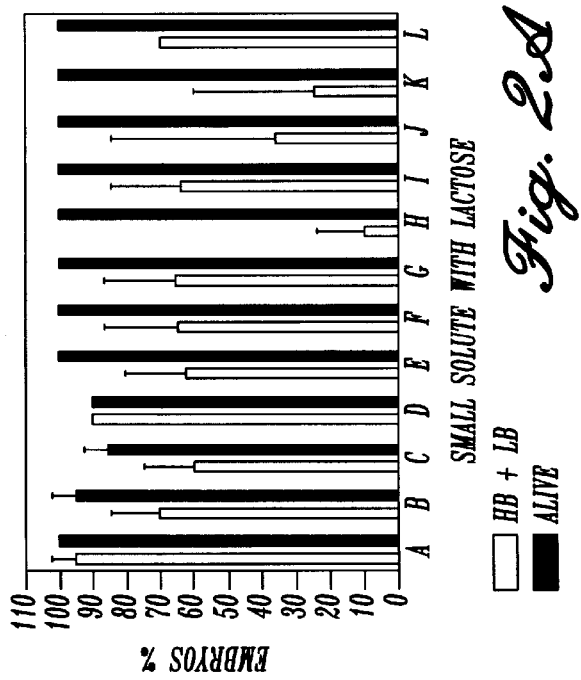
Figure 2C:
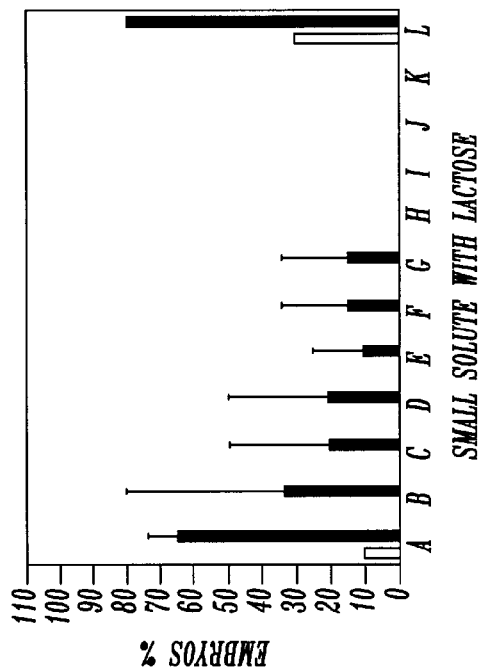
Figure 3A:
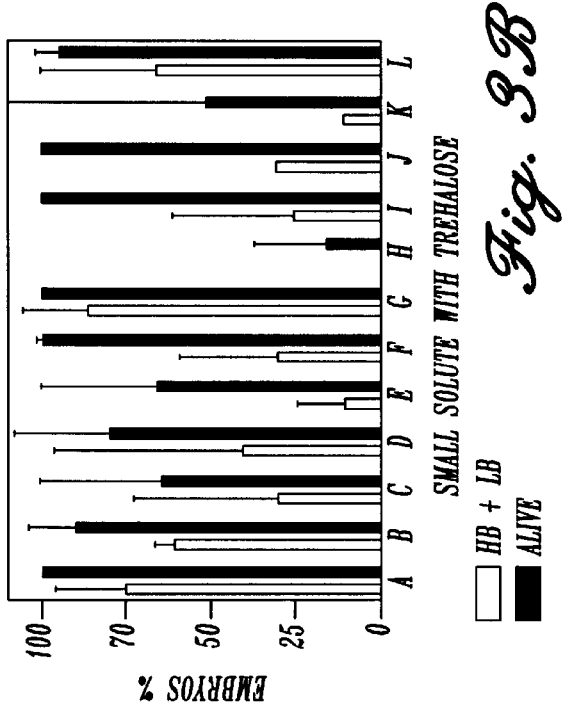
FIGS. 3A, B and C illustrate the survival of mouse embryos following 1, 2 and 3 days of storage, respectively, at 4° C. in an aqueous solution of trehalose and various Class II solutes, together with 1.75 mM $CaSO_4$.
Figure 3B:
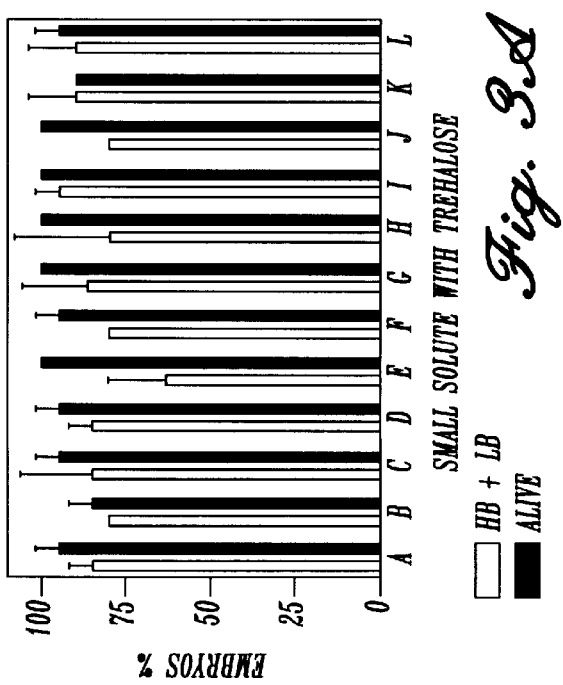
Figure 3C:
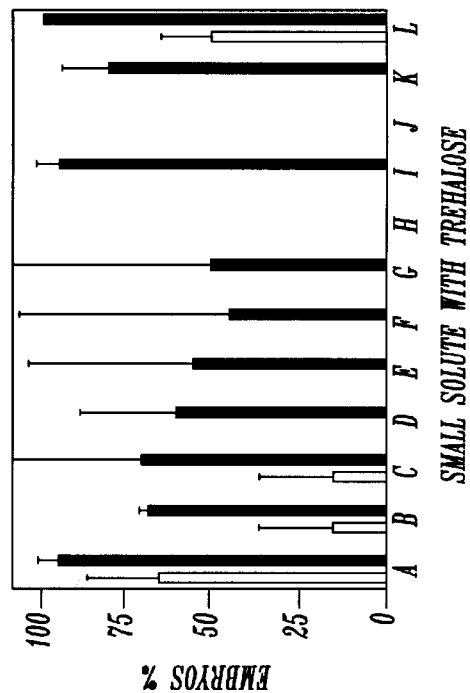
Figure 4A:
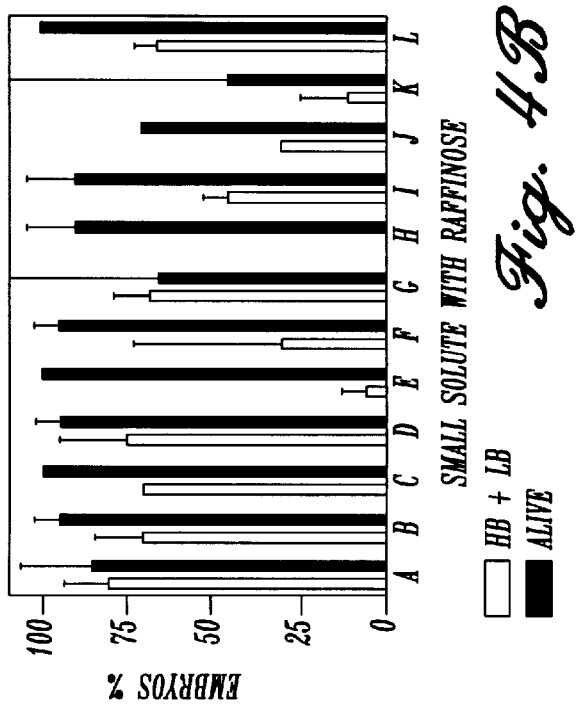
FIGS. 4A, B and C illustrate the survival of mouse embryos following 1, 2 and 3 days of storage, respectively, at 4° C. in an aqueous solution of raffinose and various Class II solutes, together with 1.75 mM $CaSO_4$.
Figure 4B:
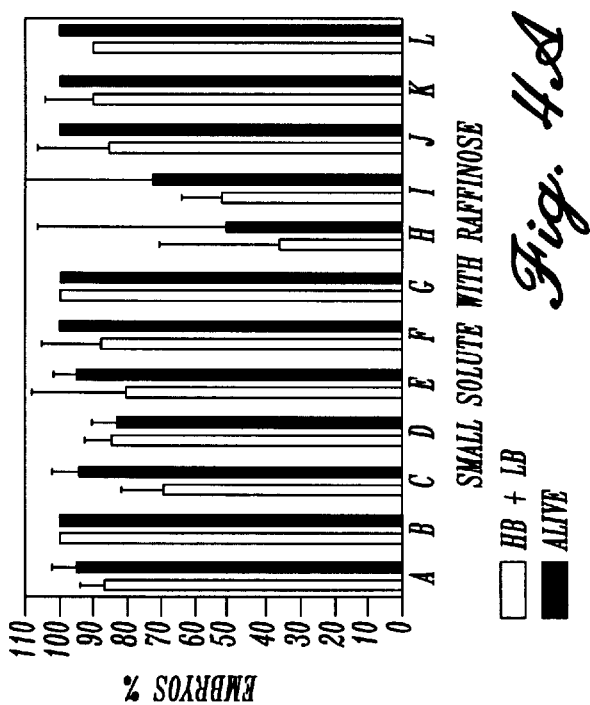
Figure 4C:
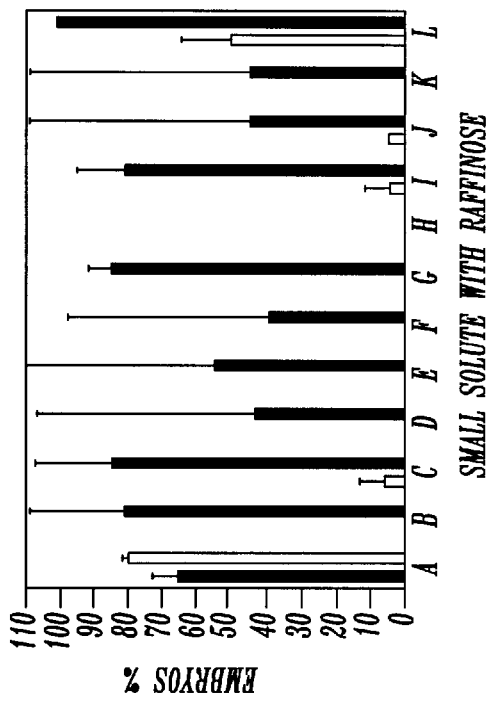

Viable mouse embryos were stored for periods of 1, 2 or 3 days at 4° C. in either PBS or an aqueous solution of either raffinose, trehalose, sucrose or lactose (Class I solutes), together with a solute selected from the group consisting of trimethyl amine oxide (TMAO), betaine, taurine, sarcosine, glucose, mannose, fructose, ribose, galactose, sorbitol, mannitol, inositol and taurine (Class II solutes), at a ratio of Class I solute to Class II solute of 1.6:1. Each Class I/Class II solution also contained calcium sulfate at a concentration of 1.75 mM. The solutions also contained 0.1–1% bovine serum albumin (BSA) and 25 mg/L of kanamycin sulfate. All reagents were obtained from Sigma Chemical Company (St. Louis, Mo.). Survival of the embryos was assessed by subsequent culture in Dulbecco's Modified Eagles Medium (DMEM, Life Technologies, Grand Island, N.Y.) and was expressed both as the number of live embryos present after storage and the number of embryos which hatched after 48 hours in culture at 37° C. The results of these experiments for solutions of sucrose, lactose, trehalose and raffinose are shown in FIGS. 1–4, respectively, wherein HB+LB represents the percentage of embryos hatched or reaching the late blastocyst stage. Specifically, FIGS. 1A, B and C illustrate the survival of mouse embryos following 1, 2 and 3 days of storage, respectively, at 4° C. in an aqueous solution of sucrose and various Class II solutes, together with 1.75 mM CaSO$_4$; FIGS. 2A, B and C illustrate the survival of mouse embryos following 1, 2 and 3 days of storage, respectively, at 4° C. in an aqueous solution of lactose and various Class II solutes, together with 1.75 mM CaSO$_4$; FIGS. 3A, B and C illustrate the survival of mouse embryos following 1, 2 and 3 days of storage, respectively, at 4° C. in an aqueous solution of trehalose and various Class II solutes, together with 1.75 mM CaSO$_4$; and FIGS. 4A, B and C illustrate the survival of mouse embryos following 1, 2 and 3 days of storage, respectively, at 4° C. in an aqueous solution of raffinose and various Class II solutes, together with 1.75 mM CaSO$_4$.

A significant percentage of embryos hatched following storage for one day in most combinations of solutes, but following three days of storage a high percentage of hatching was only obtained with combinations of raffinose, trehalose or sucrose with TMAO. Raffinose was found to be the best Class I solute and TMAO the best Class II solute, with trehalose and betaine being the second best Class I and Class II solutes, respectively. The optimal total osmolality of the Class I/Class II solutions for preservation of mouse embryos was found to be 0.30 OsM.

Figure 5B:
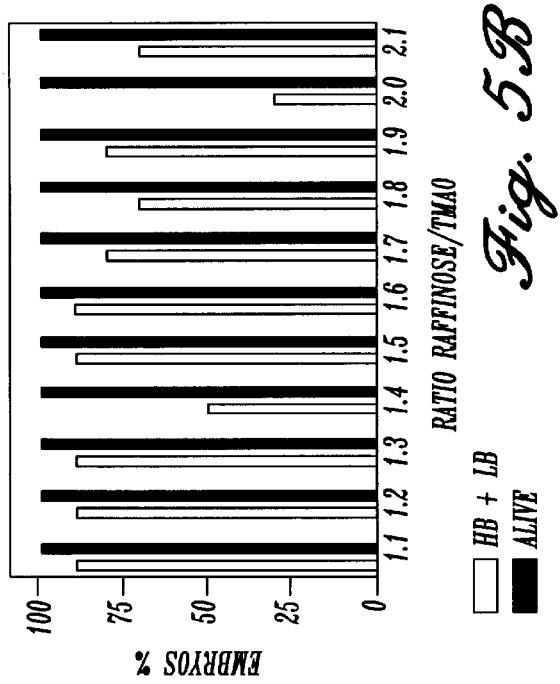
FIGS. 5A, B and C illustrate the survival of mouse embryos after storage for 1, 2 and 3 days, respectively, at 4° C. in aqueous solutions with varying molar ratios of raffinose to TMAO, with 1.75 mM $CaSO_4$.
Figure 5A:
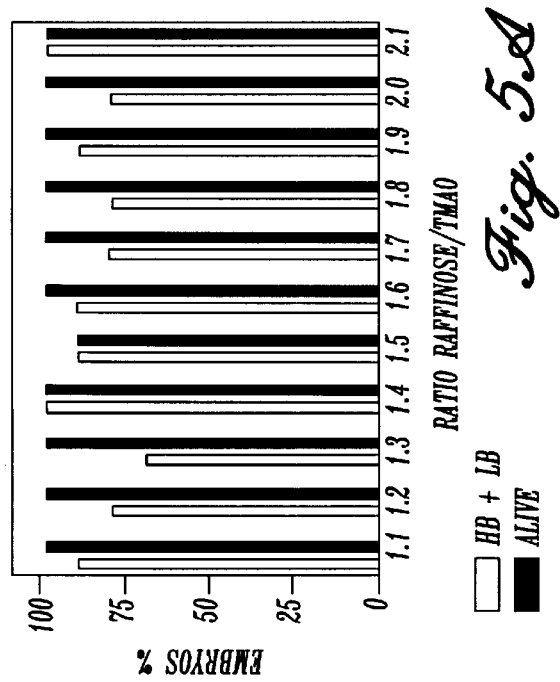
Figure 5C:
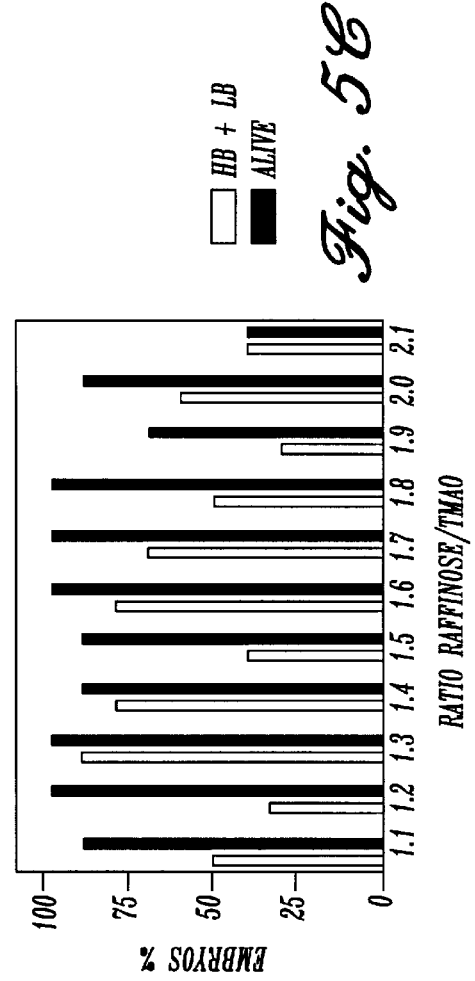

The three best combinations of Class I and Class II solutes were then retested to determine the optimal molar ratios of Class I to Class II solutes. The results of this study for raffinose and TMAO, with 1.75 mM CaSO$_4$, are shown in FIGS. 5A–C, with FIG. 5A illustrating survival after storage for 1 day, FIG. 5B illustrating survival after storage for 2 days and FIG. 5C illustrating survival after storage for 3 days. Of the three solutions tested, a raffinose:TMAO molar ratio of 1.6:1 resulted in the highest percentage of survival of embryos. The second highest percentage of survival was obtained with a trehalose:TMAO molar ratio of 1.3:1. The third highest percentage of survival was obtained with a raffinose:betaine molar ratio of 1.4:1.

Figure 6:
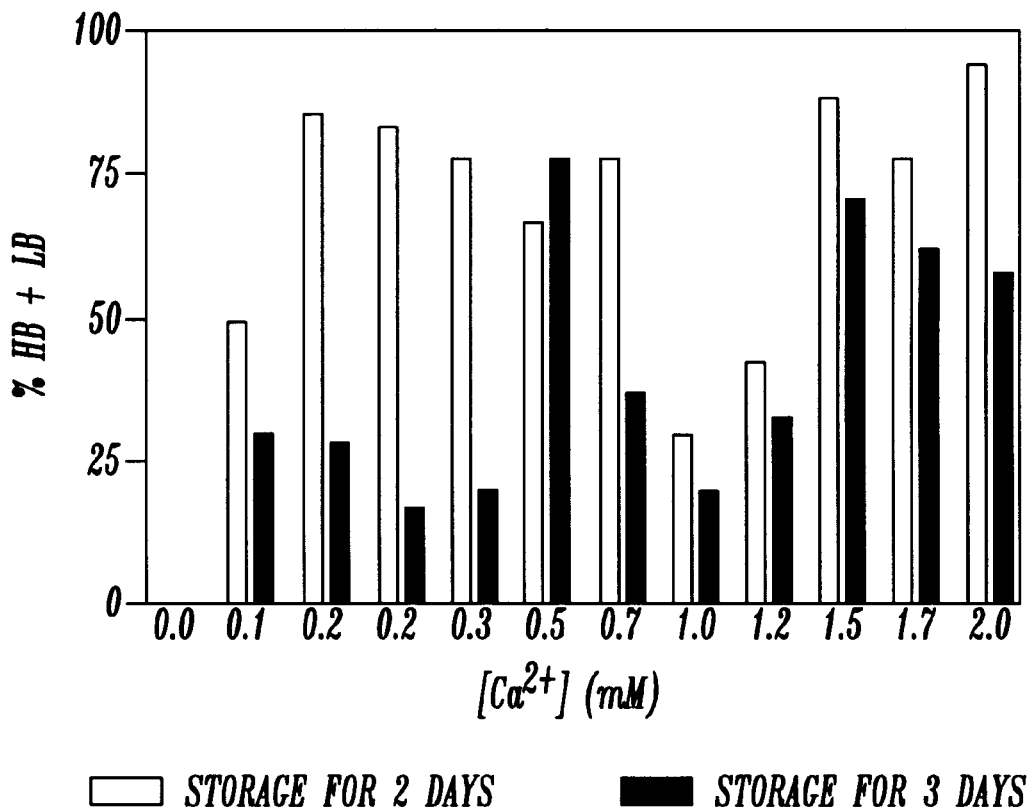
FIG. 6 shows the $Ca^{2+}$ dependence of mouse embryo survival following storage in raffinose/TMAO at 4° C. for 2 and 3 days.

The percentage of embryos hatching following storage for 2 and 3 days at 4° C. in solutions containing a 1.6:1 molar ratio of raffinose to TMAO and varying concentrations of $Ca^{2+}$ is shown in FIG. 6. It was found that $Ca^{2+}$ is required for embryo preservation, with a non-linear concentration dependence. A CaSO$_4$ concentration of 1.75 mM was subsequently used in all solutions and with most biological materials. One exception was that of isolated platelets which were found to survive best in $Ca^{2+}$-free solutions.

Figure 7D:
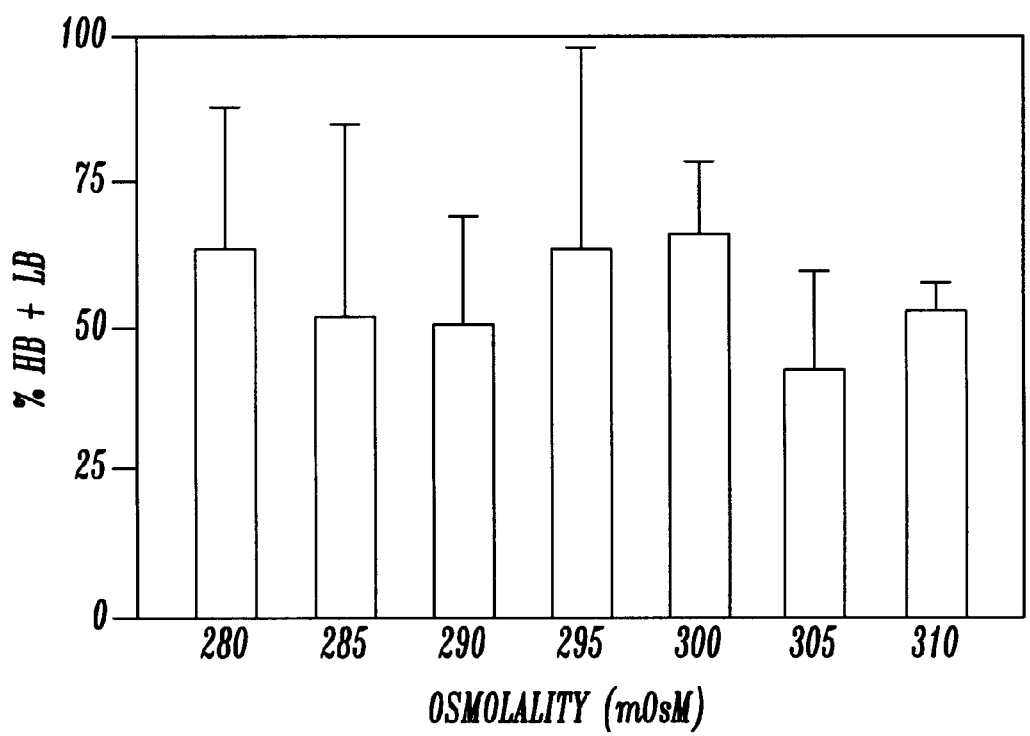
FIG. 7D shows the mean and SEM of survival of mouse embryos following 1, 2, 3 and 4 days of storage in Solution 70/30 at various osmolalities.

A raffinose/TMAO 1.6:1 solution with 1.75 mM CaSO$_4$ was then mixed in different proportions with a solution of 0.30 OsM Na$_2$SO$_4$ containing 1.75 mM CaSO$_4$. The percentage of mouse embryos hatching in culture following storage in these solutions for 1, 2 and 3 days at 4° C. are shown in FIGS. 7(i)A, B and C, respectively. The highest percentage of hatched embryos was obtained with 70% raffinose/TMAO (1.6:1), 30% Na$_2$SO$_4$ and 1.75 mM CaSO$_4$ (hereinafter referred to as Solution 70/30). FIG. 7(ii) shows the survival of embryos following storage for 1, 2, 3 and 4 days at 4° C. in Solution 70/30 of various osmolalities. The optimal osmolality appears to be close to 300 mOsM but not to be of critical importance. Solution 70/30 was subsequently used for many applications and proved to be an effective storage solution for many biological materials including bone marrow stem cells, hearts, red blood cells and osteoblasts. Solution 70/30 without $Ca^{2+}$ was found to be a preferred solution for the preservation of platelets.

In subsequent studies, mouse embryos were stored at 4° C. in a range of mixtures of equiosmolar solutions of sodium citrate and raffinose/TMAO, with the raffinose and TMAO being present at a ratio of 1.6:1. FIGS. 25A–D show the percentage of embryos that hatched in culture following storage in such solutions for 1, 2, 3 or 4 days, respectively, compared to those that hatched following storage in either PBS or Solution 70/30. These results indicate that solutions comprising sodium citrate, raffinose and TMAO may be more effective for long term storage of embryos than either PBS or Solution 70/30.

Figure 27:
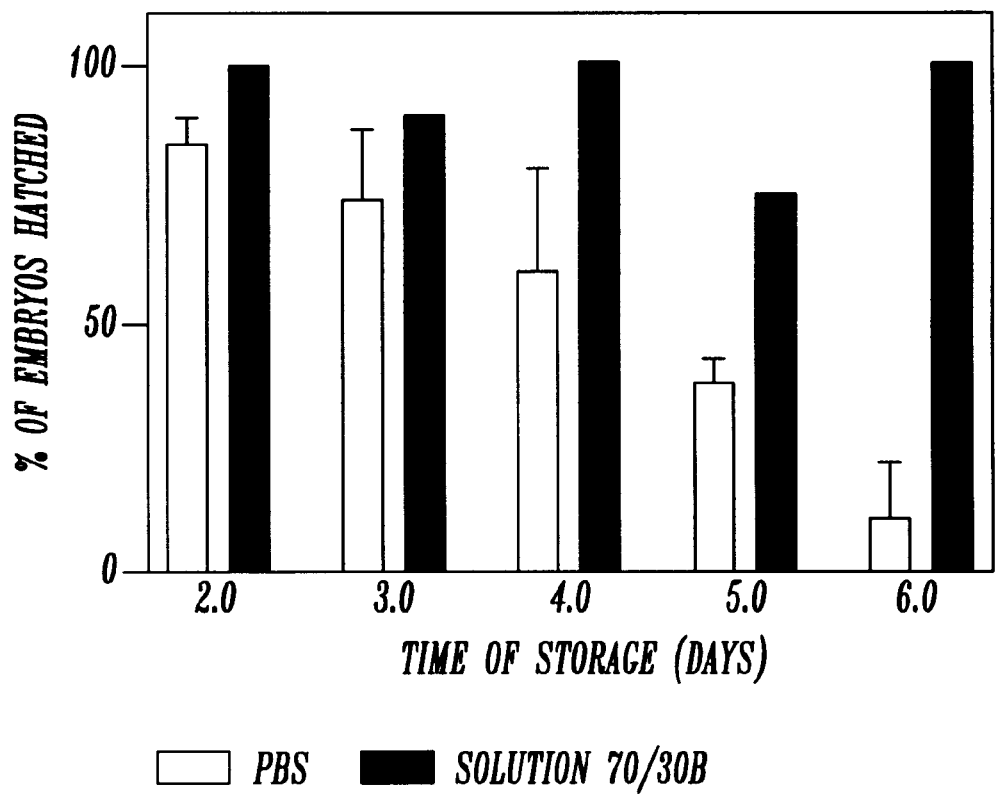
FIG. 27 shows the survival of mouse embryos following storage at 4° C. in either PBS or 30% NaCl/70% TMAO plus calcium chloride (referred to as Solution 70/30B).

FIGS. 26A–E show the percentage of mouse embryos that hatched after 3 days of culture at 37° C. following storage at 4° C. for 1, 2, 3, 4 or 5 days, respectively, in a range of mixtures of NaCl and TMAO plus calcium chloride. Solutions containing between about 20% and about 40% NaCl were found to be highly effective in preserving the viability of the embryos. FIG. 27 compares the results of storage of mouse embryos in 30% NaCl/70% TMAO plus 1.75 mM calcium chloride (referred to as Solution 70/30B) for up to 6 days at 4° C. with storage in PBS. These results demonstrate that Solution 70/30B is much more effective than PBS in preserving the viability of mouse embryos.

EXAMPLE 2

As described below, survival of mouse embryos in storage was found to be greatly enhanced by pretreatment with either a Class II solute or sodium butyrate.

Figure 8A:
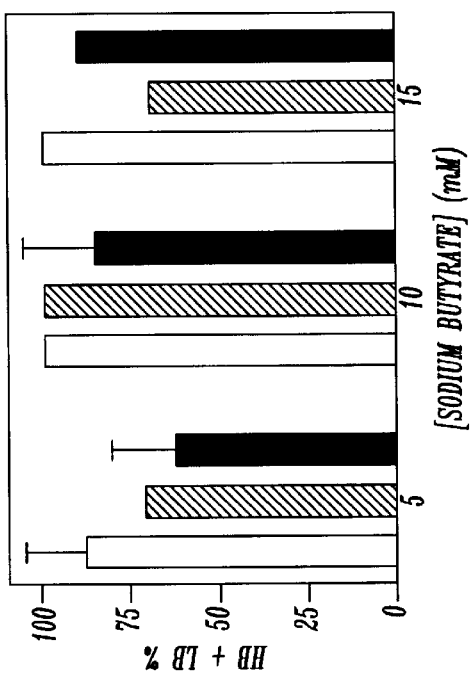
FIGS. 8A, B and C show the percentage of mouse embryos reaching the late blastocyst stage following storage for 1, 2 and 3 days, respectively, at 4° C. in Solution 70/30 after pretreatment with 5, 10 or 15 mM sodium butyrate in PBS at room temperature for 10, 20 or 30 minutes.
Figure 8B:
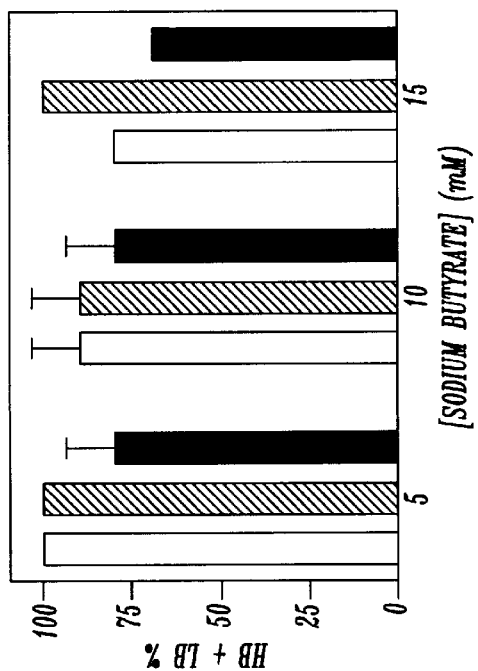
FIGS. 8D, E and F show the percentage of mouse embryos alive following storage for 1, 2 and 3 days, respectively, at 4° C. in Solution 70/30 after pretreatment with 5, 10 or 15 mM sodium butyrate in PBS at room temperature for 10, 20 or 30 minutes.
Figure 8C:
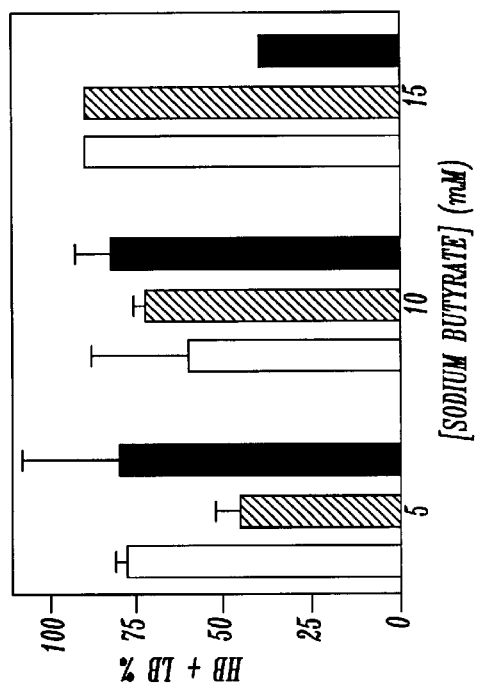
Figure 9:
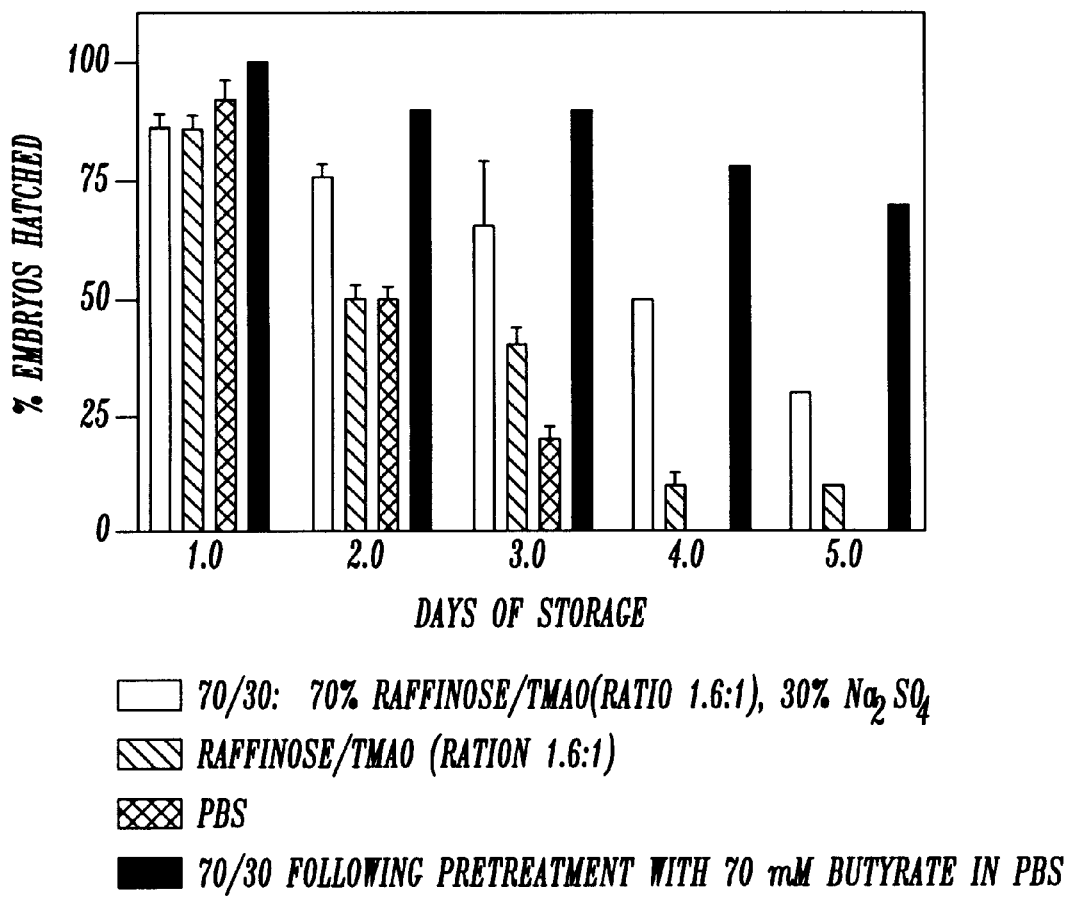
FIG. 9 shows the survival of mouse embryos following storage at 4° C. in PBS, raffinose/TMAO (ratio 1.6:1), or Solution 70/30, with and without pretreatment with 70 mM butyrate in PBS.
Figure 10A:
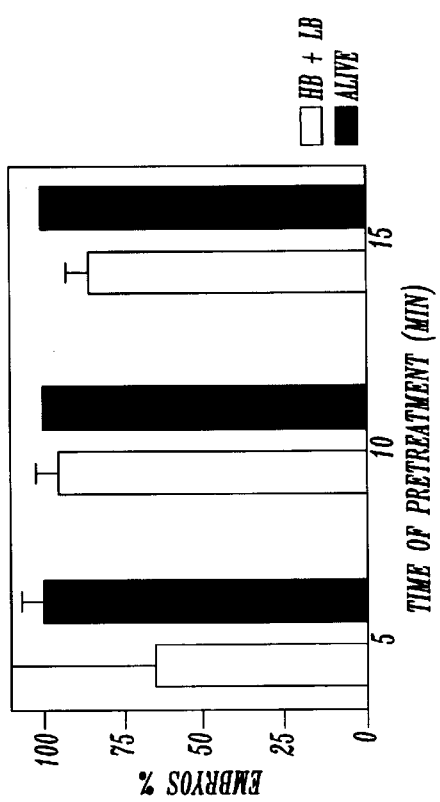
FIGS. 10A, B, C and D show the survival of mouse embryos after storage in Solution 70/30 for 1, 2, 3 and 4 days respectively following pretreatment with 25 mM sodium butyrate in PBS for 5, 10, or 15 minutes.
Figure 10B:
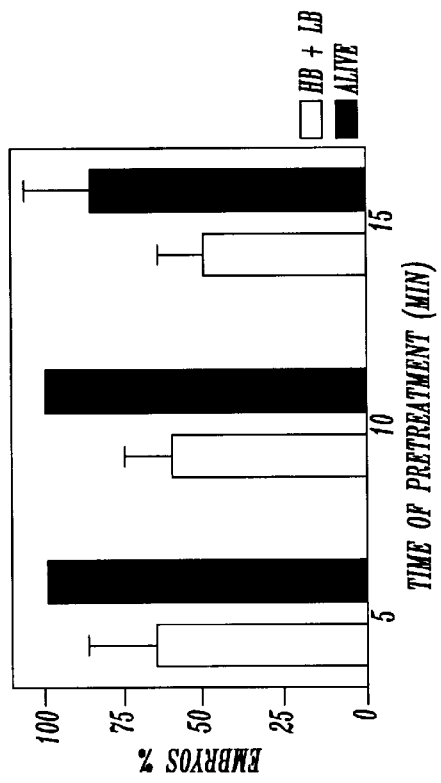
Figure 10C:
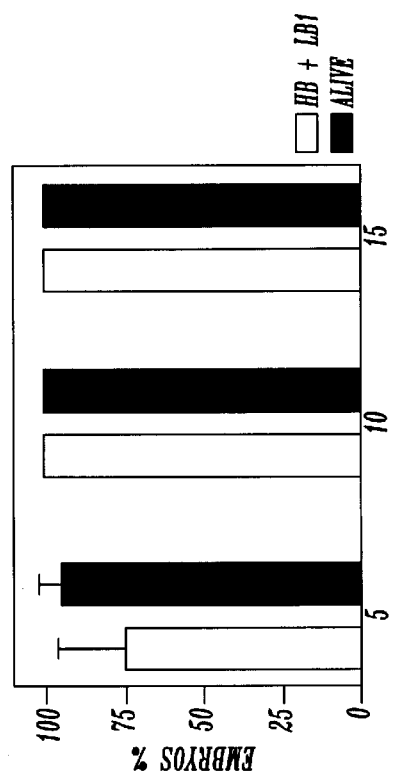
Figure 10D:
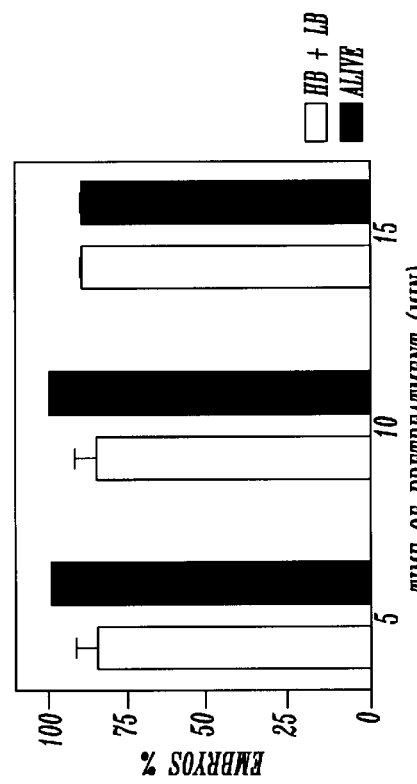

Mouse embryos were incubated with either sodium butyrate or a Class II solute at either room temperature, 30° C. or 4° C. prior to storage in Solution 70/30 for up to five days at 4° C. Many different combinations of concentrations of sodium butyrate (5–70 mM) and times of pretreatment (5–30 minutes) at room temperature gave significantly improved storage times. Sodium butyrate replaced sodium chloride at the same concentration in PBS. FIGS. 8A, B and C show the percentage of mouse embryos hatching after 1, 2 and 3 days, respectively, in storage following pretreatment with sodium butyrate at concentrations of 5, 10 or 15 mM for either 10, 20 or 30 minutes. FIGS. 8D, E and F show the percentage of mouse embryos alive after 1, 2 and 3 days, respectively, in storage following pretreatment with sodium butyrate at concentrations of 5, 10 or 15 mM for either 10, 20 or 30 minutes. Pretreatment with sodium butyrate allowed up to 80% of embryos to hatch following three days of storage in Solution 70/30. After 5 days of storage in Solution 70/30 following pretreatment with higher concentrations of sodium butyrate, up to 70% of embryos hatched compared to 2% with no pretreatment (see FIG. 9). Embryos stored in PBS without pretreatment lasted no longer than 3 days. Pretreatment of embryos with PBS without butyrate resulted in significant loss of embryos. FIGS. 10A, B, C and D show the survival of mouse embryos after up to four days of storage in Solution 70/30 at 4° C. following pretreatment with 25 mM sodium butyrate for 5, 10 or 15 minutes at room temperature.

EXAMPLE 3

The efficacy of Solution 70/30 in the storage of whole blood was investigated as detailed below.

Whole blood was diluted 1:1 by volume with either plasma, $Ca^{2+}$-containing Solution 70/30 or $Ca^{2+}$-free Solution 70/30, and stored at 4° C. for periods of up to 28 days. In the presence of citrate-based anticoagulant solutions, platelets decreased to about 30% of their initial numbers in 18 days. When EDTA was used as the anticoagulant, platelet numbers stayed in the normal range, i.e. close to about 60% survival, in $Ca^{2+}$-free Solution 70/30 but not in $Ca^{2+}$-containing Solution 70/30 or plasma.

In the same tests, white cells survived little better than platelets in a citrate-based anticoagulant. Highest survival rates after 18 days were obtained when blood was collected into an EDTA containing bag and diluted 1:1 by volume with $Ca^{2+}$-containing Solution 70/30, compared to storage in either $Ca^{2+}$-free Solution 70/30 of plasma. This replaced the $Ca^{2+}$ necessary for white cell storage and avoided the harmful effects of citrate.

EXAMPLE 4

This example illustrates the efficacy of the preservation solutions of the present invention in storage of isolated platelets at temperatures above freezing.

Figure 11:
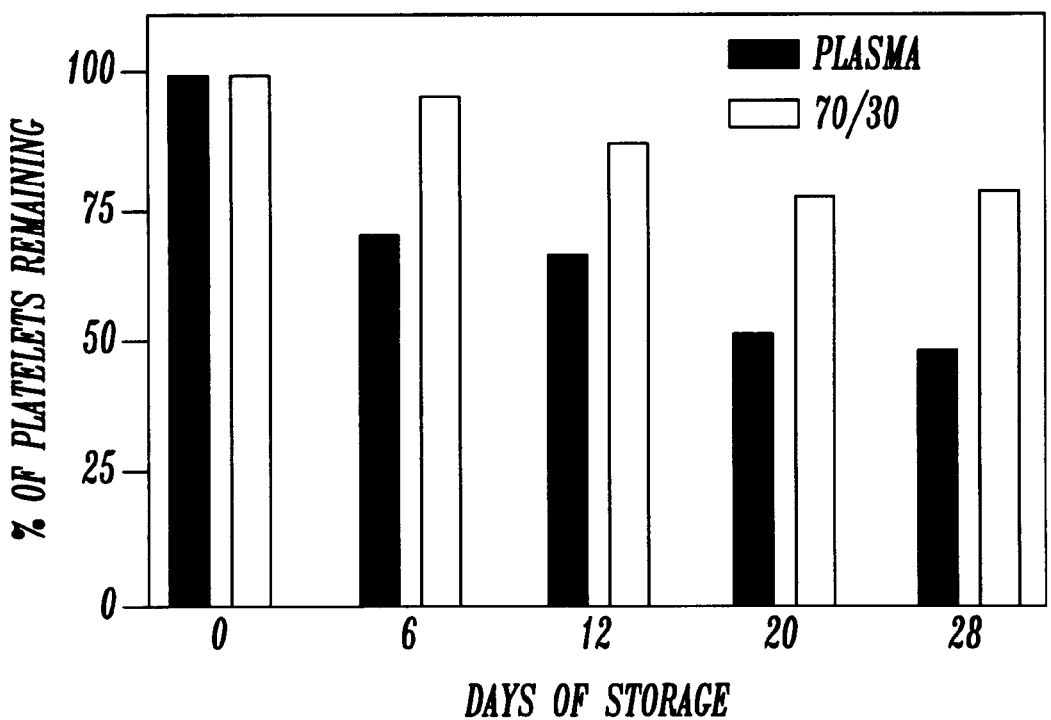
FIG. 11 shows the survival of platelets following storage at 4° C. in either plasma or $Ca^{2+}$-free Solution 70/30.

Blood was collected in EDTA and platelets isolated using standard centrifugation techniques. The final platelet-rich pellet was diluted into 50 ml of either plasma or $Ca^{2+}$-free Solution 70/30. FIG. 11 shows that 80% of platelets survived after 28 days of storage at 4 ° C. This survival rate after storage was significantly better than that in plasma and considerably better than the five days for which platelets are typically held at 21° C. The advantages of collection of blood in EDTA and avoidance of citrate, together with storage in $Ca^{2+}$-free Solution 70/30 at 4° C. are very clear.

Platelets are conventionally isolated from blood collected in citrate anticoagulant. In order to effectively preserve platelets prepared according to such methods, a preservative solution containing 45.8 mM NaCl, 184 mM TMAO and 1.96 mM sodium citrate at a total osmolality of 0.29 OsM was prepared (hereinafter referred to as Solution 70/30c2). The effectiveness of this solution in the preservation of platelets at 4° C. was assessed by counting platelets and measuring their aggregation in response to stimulation by thrombin.

Preliminary experiments showed that storage in glass tubes coated with dichlorodimethyl silane stabilized platelets relative to storage in plastic or uncoated glass. In a first experiment, platelets were first processed in tubes and subsequently stored in Solution 70/30c2 in dichlorodimethyl silane-coated glass tubes at 4° C. As shown in FIGS. 29 A and B, platelets were found to survive for 14 days with high levels of thrombin aggregation. In a second experiment, platelets were processed in plastic bags and transferred to a single dichlorodimethyl silane-coated glass bottle for storage at 4° C. in Solution 70/30c2. As shown in FIGS. 30A and B, platelet counts and thrombin aggregation levels remained high for 18 days. FIGS. 31A and B show the results of storing platelets in Solution 70/30c2 at 4° C. bags over longer periods. Although the numbers of platelets remained high after 26 days, they responded less well to thrombin activation, suggesting that the plastic surface was unfavorable.

The effectiveness of solutions of betaine, sodium chloride and sodium citrate in the preservation of platelets at temperatures above freezing was investigated as follows.

Stock solutions of 0.29 OsM betaine, 0.29 OsM NaCl and 0.1 M sodium citrate at pH 6.5, were mixed in the following proportions:

| betaine (ml) | NaCl (ml) | citrate (ml) | [betaine] (mM) | [NaCl] (mM) |
|---|---|---|---|---|
| 70 | 30 | 2 | 187 | 45.8 |
| 60 | 40 | 2 | 160 | 61 |
| 50 | 50 | 2 | 133 | 76 |
| 40 | 60 | 2 | 106 | 92 |
| 30 | 70 | 2 | 80 | 107 |

Equal volumes of platelet-rich plasma were spun down, resuspended in the above betaine/NaCl/Na citrate solutions and stored at 4 ° C. for periods of up to 7 days.

Figure 36B:
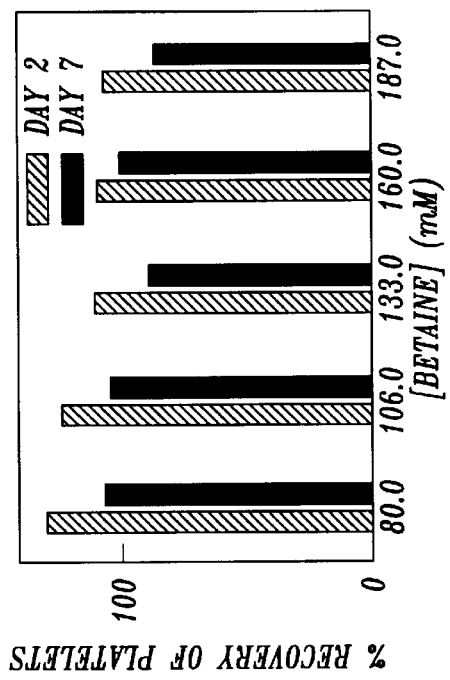
FIGS. 36A, B and C show platelet counts, percentage recovery of platelets, and percentage thrombin-activated aggregation, respectively, following storage at 4 ° C. for 0, 2 and 7 days, in solutions of NaCl, sodium citrate and varying concentrations of betaine.
Figure 36A:
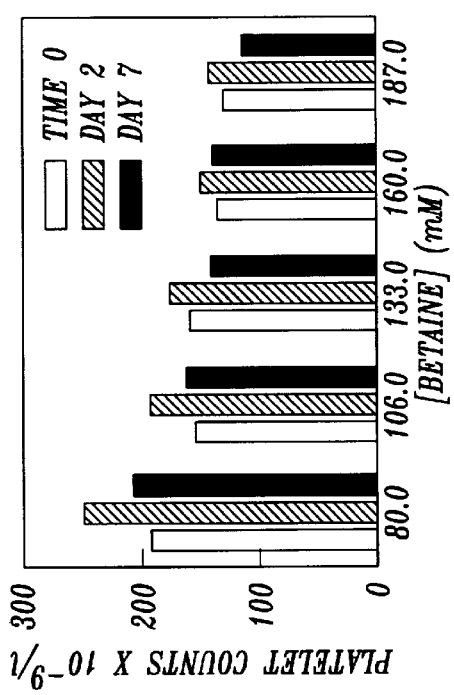
Figure 36C:
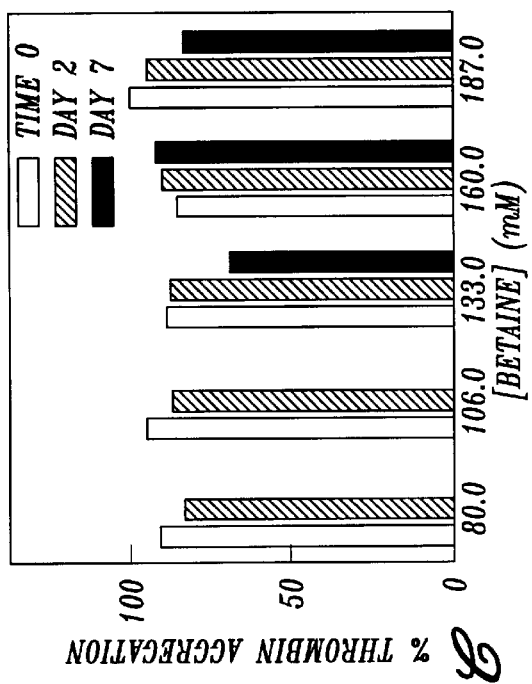

The results of this study are shown in FIGS. 36A, B, C, with FIG. 36A showing platelet counts, FIG. 36B showing percentage recovery of platelets and FIG. 36C showing percentage of thrombin-stimulated aggregation. The percentage aggregation following storage for 7 days in solutions of 80 mM and 106 mM betaine was not determined. The highest number of platelets were resuspended in the solution with the lowest concentration of betaine and the percentage recovery in this solution was also greatest. All solutions gave satisfactory levels of thrombin-activated aggregation.

EXAMPLE 5

This example illustrates the efficacy of solutions of the present invention for preservation of human bone marrow.

Bone marrow was collected in heparin from two different patients and diluted 1:1 by volume with solutions of the present invention or with a standard saline solution (Hanks buffered saline solution (HBSS), or saline-based murine culture medium (M-2)). The bone marrow was stored at 4° C. for periods ranging up to 28 days, at which time the white cell count and viability, number of colony forming units, and populations of CD34 and CD45 cells were determined.

Figure 12A:
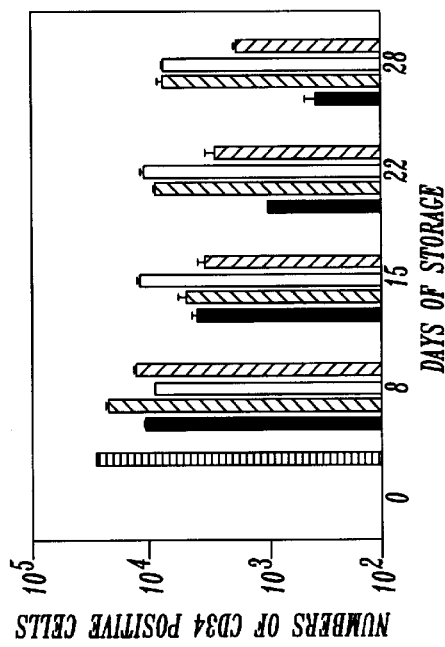
FIGS. 12A, B and C show the number of CD45- and CD34-positive cells and colony forming units, respectively, in bone marrow from patient 1 following storage in either Hanks buffered saline solution, raffinose/TMAO, trehalose/betaine or Solution 70/30.
Figure 12B:
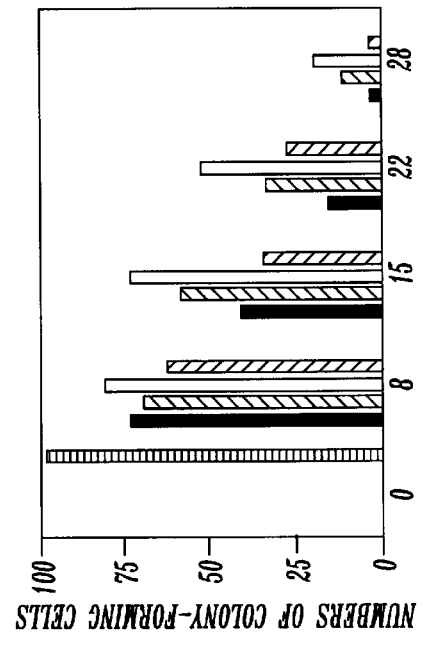
Figure 12C:
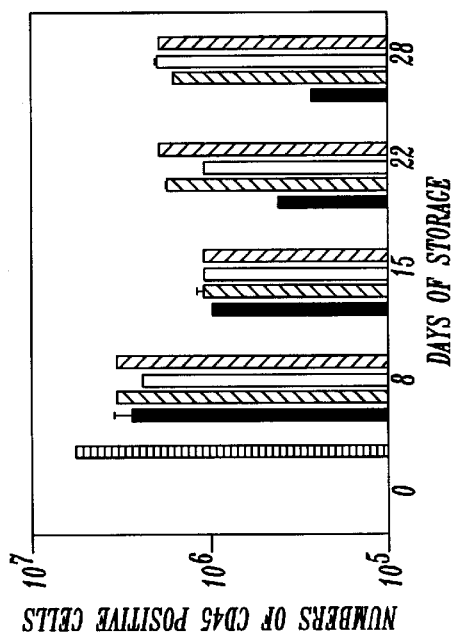

FIGS. 12A, B and C show the number of CD-45 positive and CD-34 positive cells and colony-forming units, respectively, from bone marrow harvested from patient 1 and stored in either HBSS, raffinose/TMAO, trehalose/betaine or Solution 70/30 for up to 28 days. FIGS. 13A, B and C show the number of colony-forming units, CD45-positive and CD34-positive cells, respectively, from bone marrow harvested from patient 2 and stored at 4° C. in either M2 or raffinose/TMAO with 1.75 mM $CaSO_4$. The raffinose/TMAO solution had a molar ratio of 1.6:1 and the trehalose/betaine solution had a molar ratio of 1.4:1. Solution 70/30 was particularly effective in preserving bone marrow stem cells, with the numbers of colony-forming units, CD45 and CD34-positive cells being much higher than they were in any of the control solutions, and the relative improvement increasing with time. FIGS. 13A, B and C demonstrate that the number of colony forming units, CD34-positive cells and CD-45 positive cells are significantly higher following storage in Solution 70/30 compared to storage in the saline medium M-2. The ability to store bone marrow for periods of 2–3 weeks without freezing is particularly advantageous in bone marrow transplants, since it avoids the toxicity associated with the use of DMSO in cryopreservation and allows time for a therapeutic regime, such as whole-body radiation, before re-infusion.

EXAMPLE 6

The efficacy of the inventive solutions for preservation of murine bone marrow cells was determined as follows.

Figure 14A:
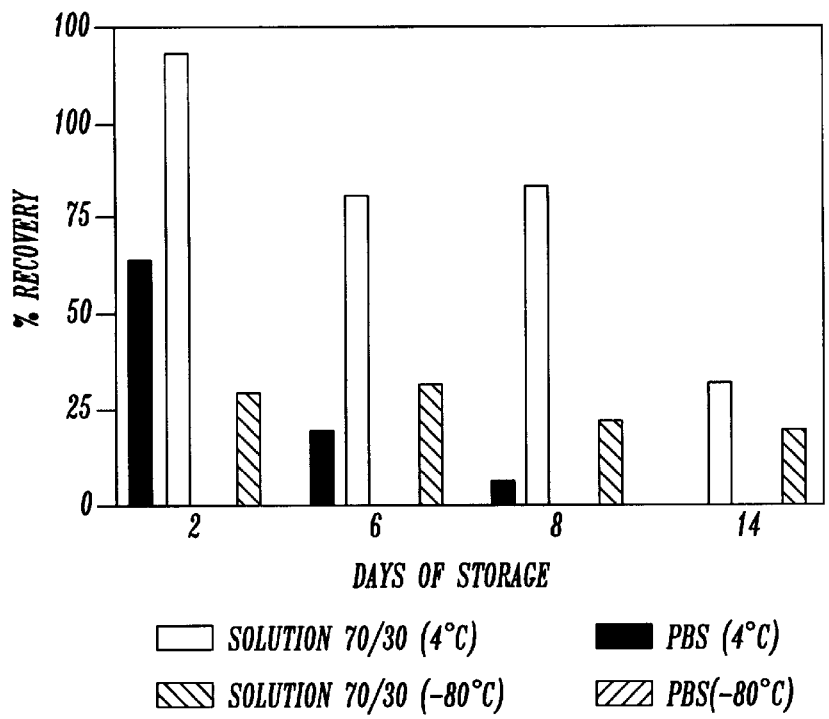
FIG. 14A shows the percentage recovery of murine bone marrow cells stored in PBS or Solution 70/30 at either 4° C. or –80° C.

Murine bone marrow was harvested directly into Solution 70/30 or into PBS. The resulting solutions were stored either at 4° C. or −80° C. FIG. 14A shows that murine bone marrow stored in Solution 70/30 at 4° C. showed 28% recovery after 14 days, with no bone marrow cells stored at 4° C. in PBS for 14 days surviving. Bone marrow frozen in Solution 70/30 at −80° C. showed 20% recovery after 8 and 14 days, whereas no bone marrow cells frozen in PBS at −80° C. for 2, 6, 8 and 14 days survived.

Figure 14B:
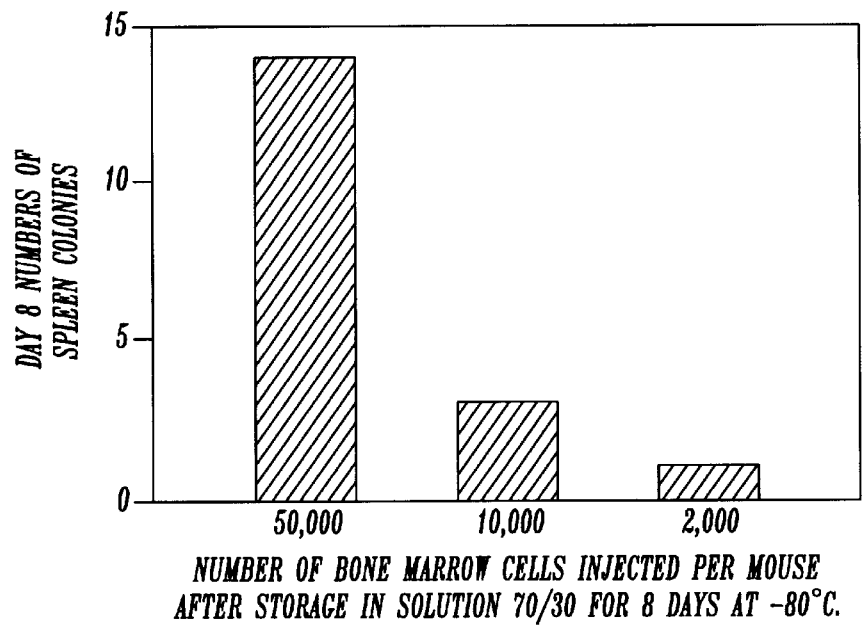
FIG. 14B shows the number of cell colonies found in spleens of lethally irradiated mice 8 days after injection of thawed murine bone marrow cells which had been stored in Solution 70/30 for 8 days at –80° C.

FIG. 14B shows that murine bone marrow frozen in Solution 70/30 at −80° C. for 8 days, thawed and then injected into lethally irradiated (1000R) syngeneic mice, developed spleen colonies when analyzed eight days after injection. Mice injected with 50,000 bone marrow cells developed sixteen colonies, mice injected with 10,000 cells developed four colonies, and one mouse injected with 2,000 bone marrow cells developed two colonies.

Figure 15:
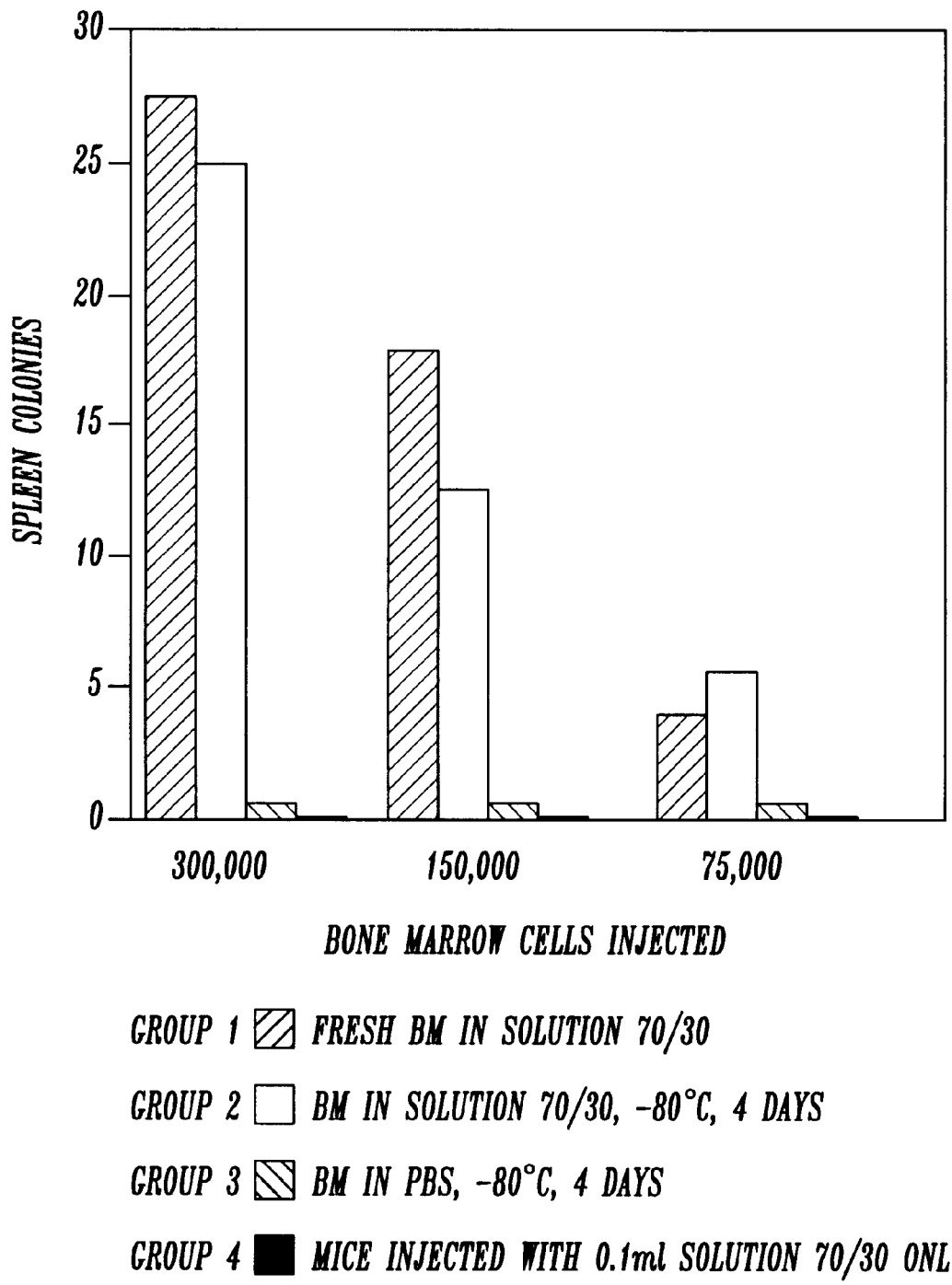
FIG. 15 shows the number of cell colonies found in spleens of lethally irradiated mice 9 days after injection with either fresh murine bone marrow cells, murine bone marrow cells stored in Solution 70/30 at –80° C. for 4 days, murine bone marrow cells stored in PBS at –80° C. for 4 days, or 0.1 ml Solution 70/30 with no cells.
Figure 16:
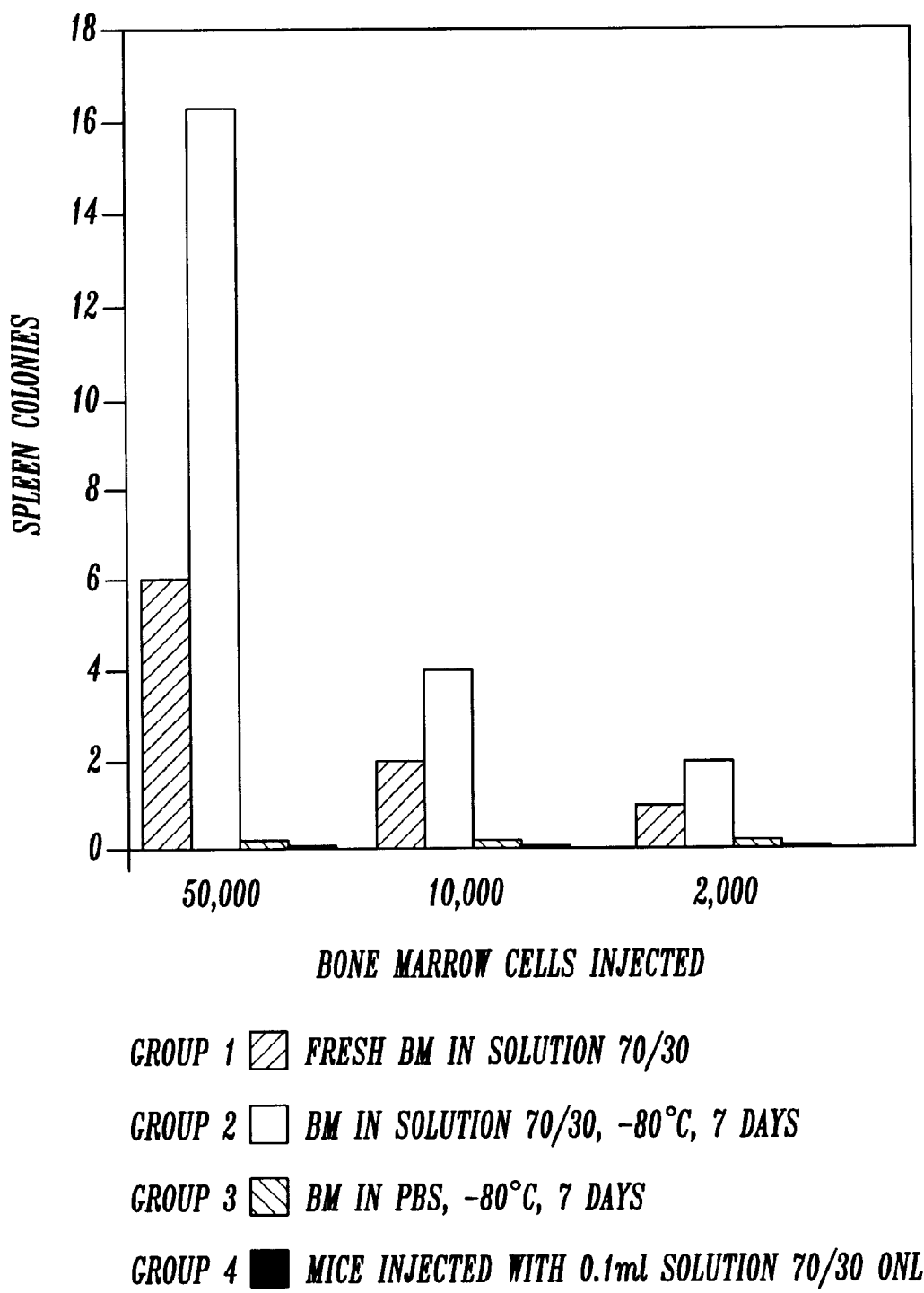
FIG. 16 shows the number of cell colonies found in spleens of lethally irradiated mice 10 days after injection with either fresh murine bone marrow cells, murine bone marrow cells stored in Solution 70/30 at –80° C. for 7 days, murine bone marrow cells stored in PBS at –80° C. for 7 days, or 0.1 ml Solution 70/30 with no cells.
Figure 17:
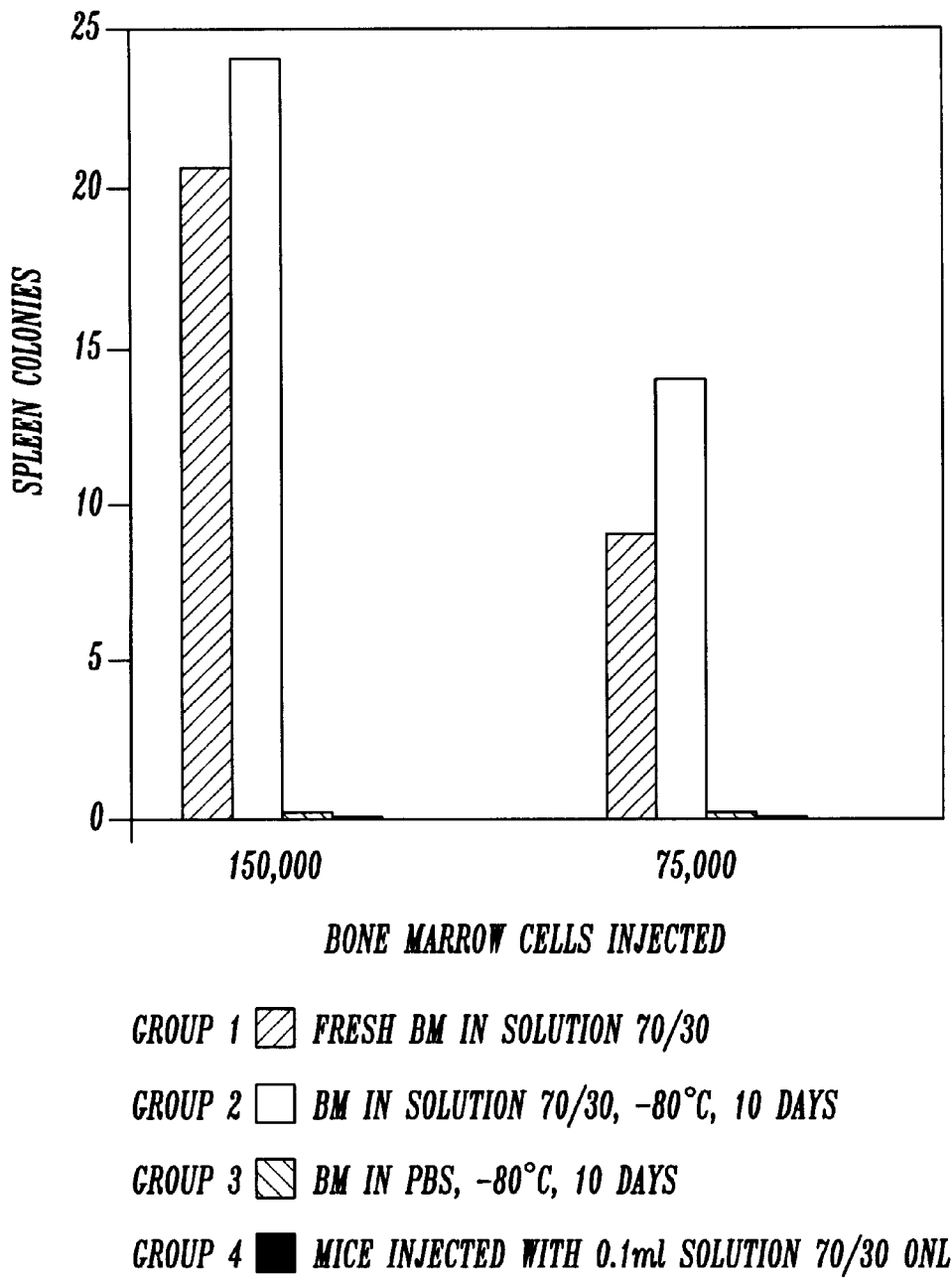
FIG. 17 shows the number of cell colonies found in spleens of lethally irradiated mice 10 days after injection with either fresh murine bone marrow cells, murine bone marrow cells stored in Solution 70/30 at –80° C. for 10 days, murine bone marrow cells stored in PBS at –80° C. for 10 days or 0.1 ml Solution 70/30 with no cells.

FIGS. 15, 16 and 17 show the effects of freezing murine bone marrow at −80° C. in Solution 70/30 or phosphate-buffered saline (PBS) for 4–10 days on the survival of haematopoietic stem cells, as determined by the ability to form spleen colonies 9–10 days after injection into lethally irradiated mice. Bone marrow was collected from the femurs of donor 6–8 week old BALB/c mice directly into Solution 70/30, or into phosphate-buffered saline (PBS) in 15 ml sterile polypropylene centrifuge tubes. These tubes were placed in a freezer at −80° C. After 4 days (FIG. 15), 7 days (FIG. 16) and 10 days (FIG. 17) tubes containing bone marrow in Solution 70/30 or PBS were removed from the freezer and thawed at room temperature. Viable cell numbers were determined.

To determine haematopoietic stem cell activity in the frozen and thawed bone marrow, recipient BALB/c mice (6–10 weeks old) were lethally irradiated and divided into four groups, each group containing four mice. In addition, fresh bone marrow was collected from healthy donor BALB/c mice into Solution 70/30. The four groups of irradiated recipient mice were injected intravenously with 0.1 ml of the following:

Group 1: fresh bone marrow cells collected directly in Solution 70/30;

Group 2: identical numbers of bone marrow cells collected in Solution 70/30 and frozen at −80° C.;

Group 3: identical numbers of bone marrow cells collected in PBS and frozen at −80° C.;

Group 4: Solution 70/30 lacking bone marrow cells.

The number of bone marrow cells injected is shown in each figure. The data demonstrate that murine haematopoietic stem cells survive freezing in Solution 70/30 at −80° C. for periods of up to 10 days and retain in vivo spleen colony forming properties.

The following murine and human haematopoietic tumor cell lines were resuspended in Solution 70/30 and frozen at −80° C. for periods of from 2 to 10 days: P3 (murine plasmacytoma); SP2/0 (murine plasmacytoma); EL4 (murine T cell lymphoma); Jurkat (human T cell lymphoma); HL60 (human monocytic tumor); and K562 (human early haematopoietic tumor). Upon thawing at room temperature and analysis for viable cells, either by uptake of trypan blue, or by the ability to grow in mammalian tissue culture medium supplemented with fetal bovine serum at 37° C., no cells were observed to survive freezing at −80° C.

The ability of the inventive solutions to purge murine bone marrow of leukemic cells was demonstrated as follows. Fresh bone marrow cells from BALB/c mice were collected in Solution 70/30 at a concentration of $10^7$ cells per ml. SP2/0 cells were also prepared in Solution 70/30 at a concentration of $10^7$ cells per ml. Three groups of cells were prepared for freezing at −80° C.:

Group 1: bone marrow cells in Solution 70/30;

Group 2: a mixture of equal parts of bone marrow and SP2/0 cells in Solution 70/30; and Group 3: SP2/0 cells alone in Solution 70/30.

Figure 18:
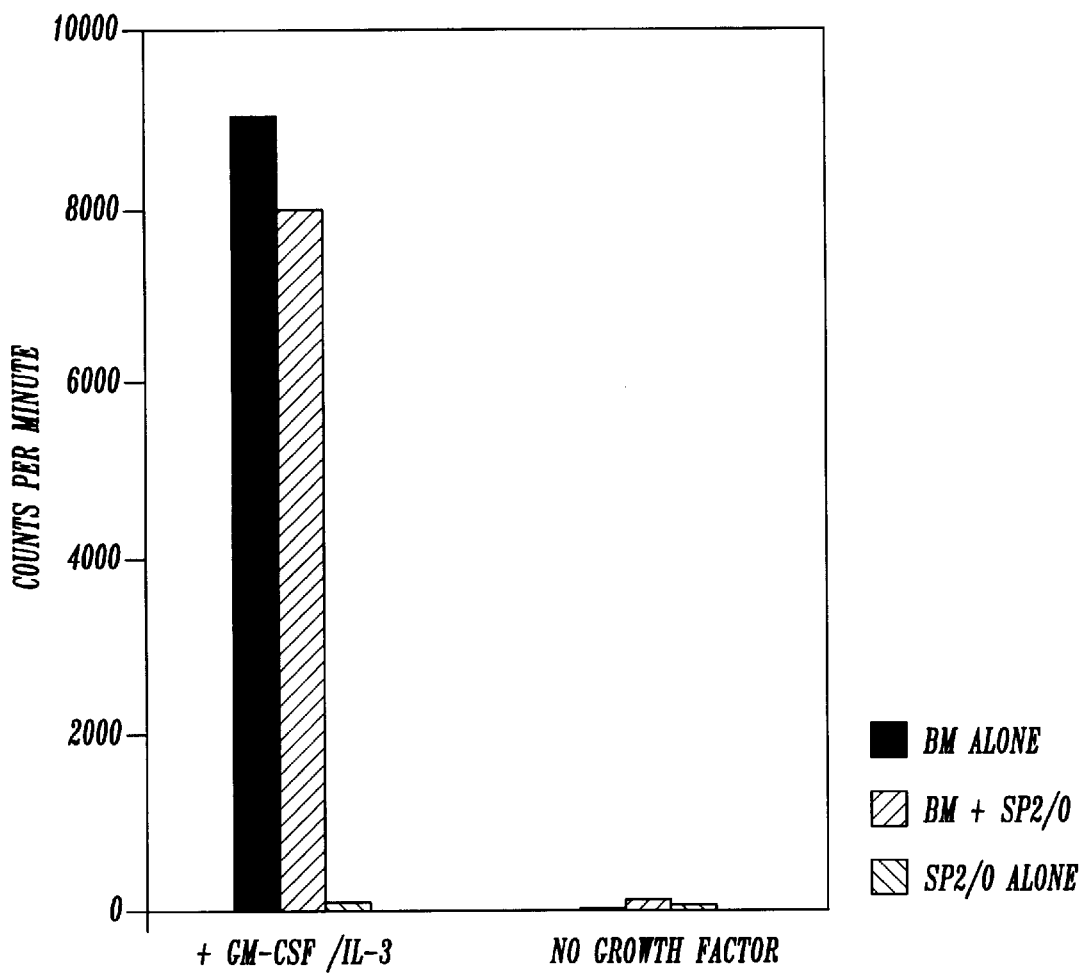
FIG. 18 shows the uptake of tritiated thymidine by murine bone marrow cells, leukemiac SP2/0 cells, and a mixture of murine bone marrow cells and SP2/0 cells, following storage in Solution 70/30 at –80° C. for 4 days.

After 4 days, cells were thawed at room temperature, collected by centrifugation and resuspended in mammalian tissue culture medium containing 5% fetal bovine serum, 20 ng/ml of murine granulocyte-macrophage colony stimulating factor (GM-CSF) and 20 ng/ml of Interleukin-3 (IL-3). Cells were incubated at 37° C. in an incubator gassed with 10% $CO_2$ in air. After 4 days, cells were incubated with 1 $\mu$C per ml of radioactive thymidine for 24 hours, and uptake was measured and expressed as counts per minute. As shown in FIG. 18, bone marrow cells alone survived storage in Solution 70/30 at −80° C., whereas the SP2/0 cells did not survive storage under these conditions. In the mixture of bone marrow and SP2/0 cells, only the bone marrow cells survived.

EXAMPLE 7

The efficacy of the inventive solutions for preservation of hearts was determined as follows.

Figure 19:
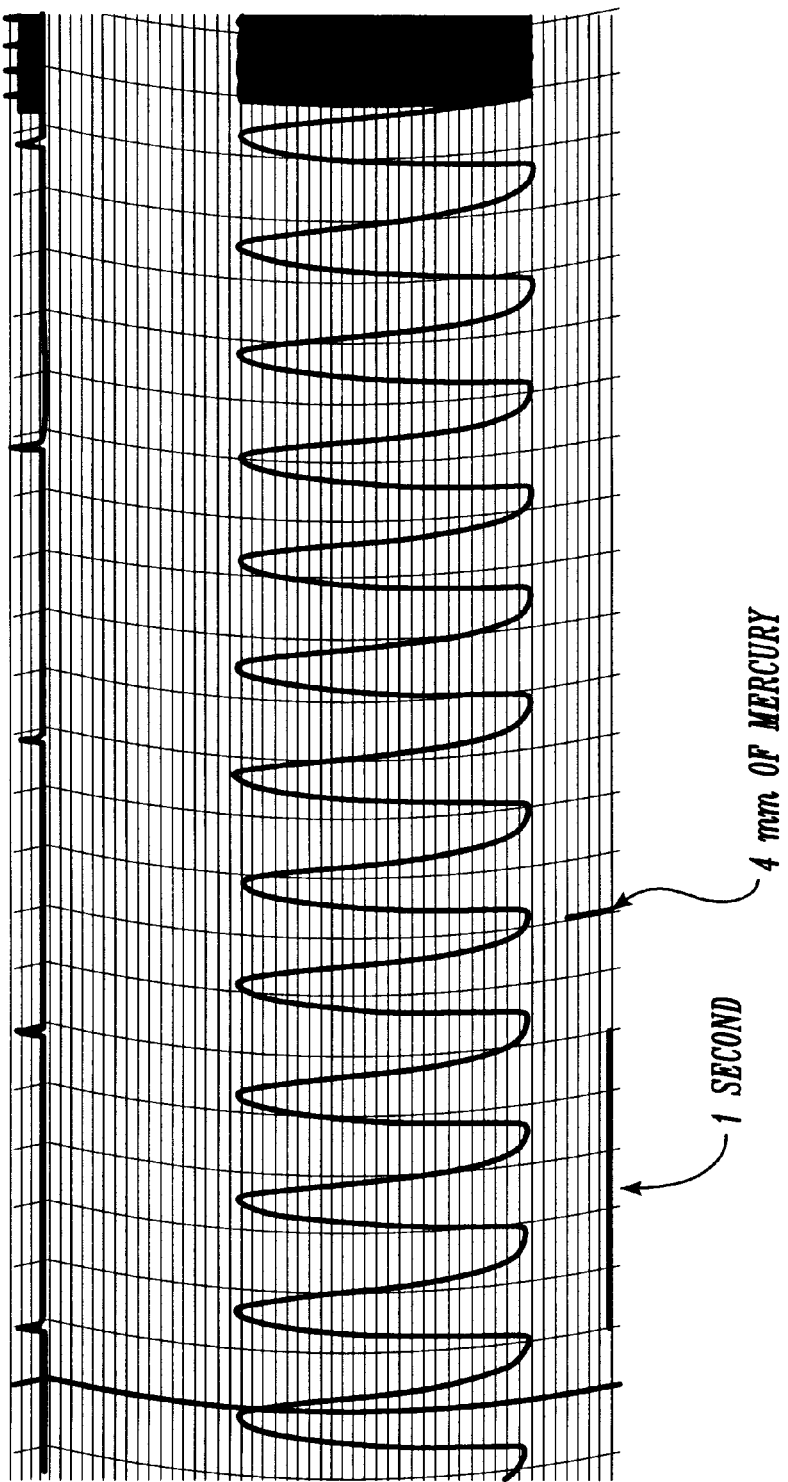
FIG. 19 shows a trace from a pressure transducer for a rat heart following storage for 4 hours at 4° C. in Solution 70/30.

Rat hearts were surgically removed and perfused through the aorta with either Solution 70/30 or raffinose/TMAO (molar ratio 1.6: 1) at 4° C., during which time the heart rate fell from about 300 beats per minute to about 180 beats per minute. The hearts were then stored in the same solution for between 4 to 24 hours, during which time the hearts stopped beating. The hearts were subsequently remounted on a cannula and reperfused with Krebs solution initially at room temperature rising to 37° C. over 20 minutes. Using only gravity feed of the perfusing solutions, recovery of hearts after 4 hours of storage was excellent, with both heart rate and developed pressure in the normal range (heart rate 170 beats/minute, pressure 98 mm mercury; see FIG. 19). When pumps were used in perfusion, variable results were obtained. In general, the pressure exerted by the pump on the heart was found to be damaging, with the damage often being irreversible.

Storage for periods longer than 4 hours was achieved by pretreating the heart with 25 mM taurine in Krebs solution for 10 minutes at 38° C. before perfusion with cold Solution 70/30 or raffinose/TMAO and storage at 4° C. With only gravity feed for the initial perfusion and the reperfusion, hearts stored for 24 hours recovered heart rate in the normal range and pressure approximately half the normal level. Subsequent experiments showed that pretreatment with taurine could be avoided by adding approximately 0.2 mM taurine to the storage solution to prevent efflux of endogenous taurine.

Figure 28:
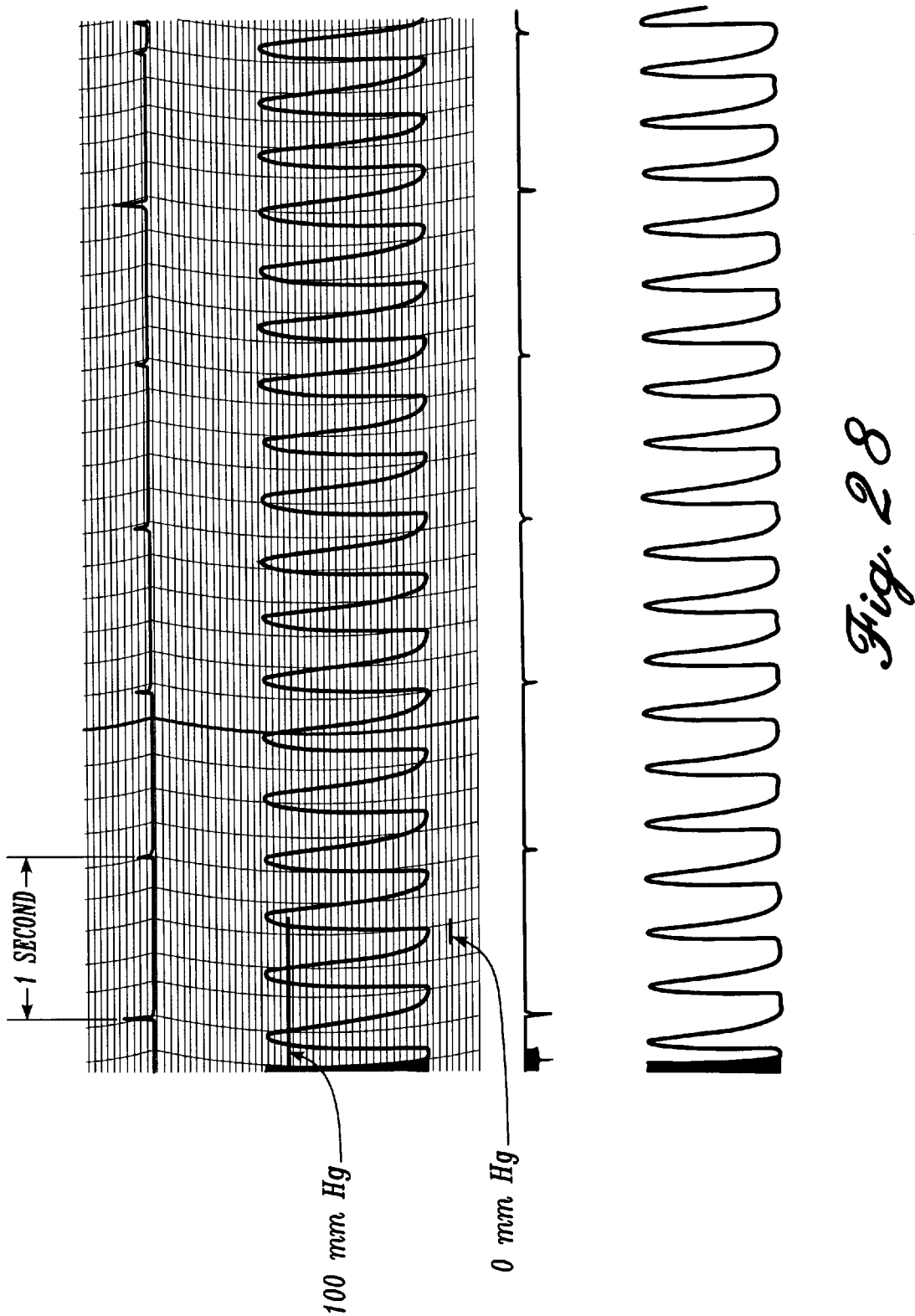
FIG. 28 shows traces from a pressure transducer for a freshly excised rat heart (upper trace) and for a rat heart following storage at 4° C. in Solution 70/30B (lower trace).

In further studies, a rat heart was excised directly into a solution of 30% 290 mOsM NaCl, 70% 290 mOsM TMAO and 1.75 mM $CaCl_2$ (Solution 70/30B) at 4° C., trimmed, then cannulated at the aorta and perfused with oxygenated Solution 70/30B at 4° C. until the blood was displaced. The heart was quickly placed in 20 ml of oxygenated Solution 70/30B at 4° C. and pressurized with 25 ml air. All these steps were carried out under sterile conditions. After 17–20 hours of storage at 4° C., the heart was recannulated at the aorta and perfused with Krebs solution at 37° C. using gravity feed with a pressure of 100 ml water. The atria began to beat visibly immediately. Ventricles were slower to start with the beat strengthening with time over approximately 30 minutes, at which point a pressure transducer was inserted and heart rate and ventricular pressure was recorded on a Grass recorder. Hearts subjected to this procedure kept beating for at least two hours. FIG. 28 shows traces for a freshly excised heart (upper trace) and for one that had been stored in Solution 70/30B for 17 hours at 4° C. (lower trace). Four hearts gave similar traces in or near the normal range. A fifth heart, which had a faster heart beat and appeared to have as strong a ventricular pressure, was damaged by insertion of the pressure-transducing catheter so no trace could be obtained.

The results obtained using the storage solutions of the present invention compare favorably with the prior art technique of preserving hearts in cold saline-based media, wherein the heart can only be stored for 5 hours or less due to unacceptable deterioration of biological function. Storage of a heart for 24 hours without deterioration would allow time for its transport for transplantation worldwide.

EXAMPLE 8

Figure 20:
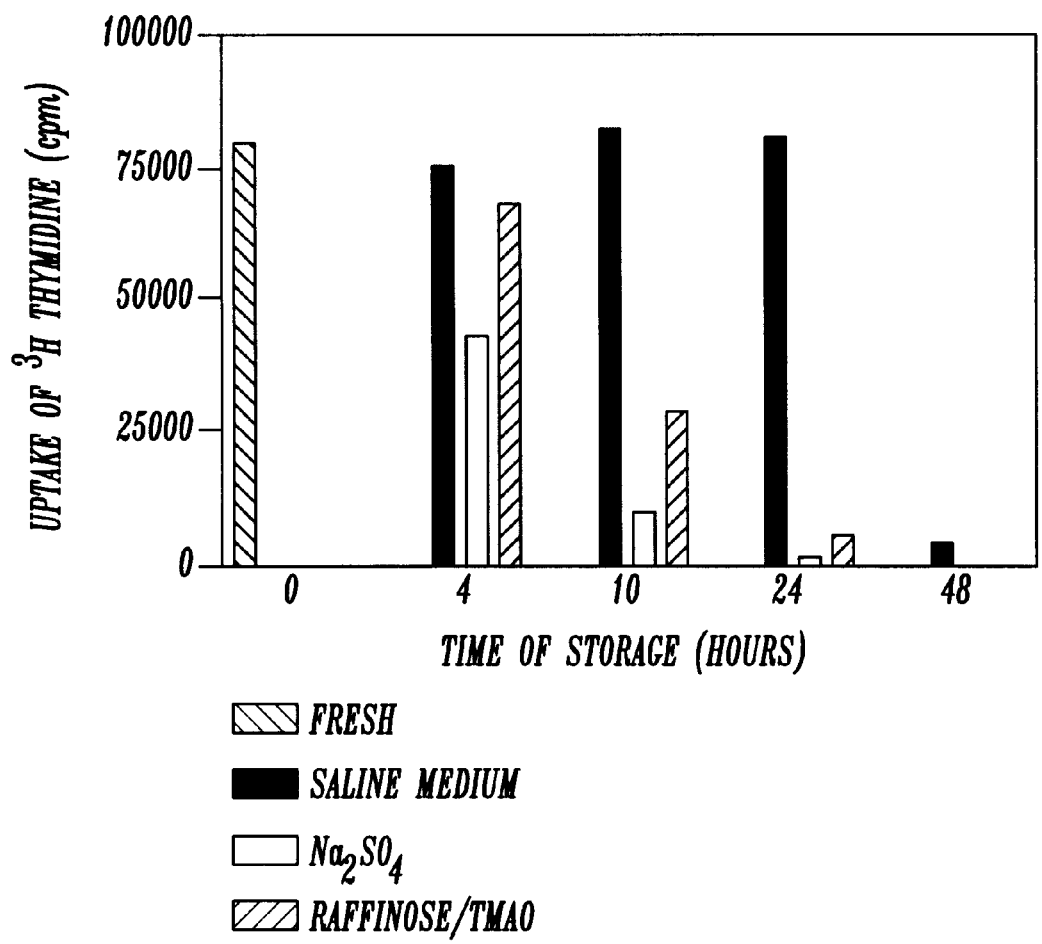
FIG. 20 shows the proliferation of Jurkat cells (acute T-cell leukemia) assessed by uptake of tritiated thymidine, following storage at 4° C. in saline or in preservation solutions of the present invention for up to 48 hours.
Figure 21:
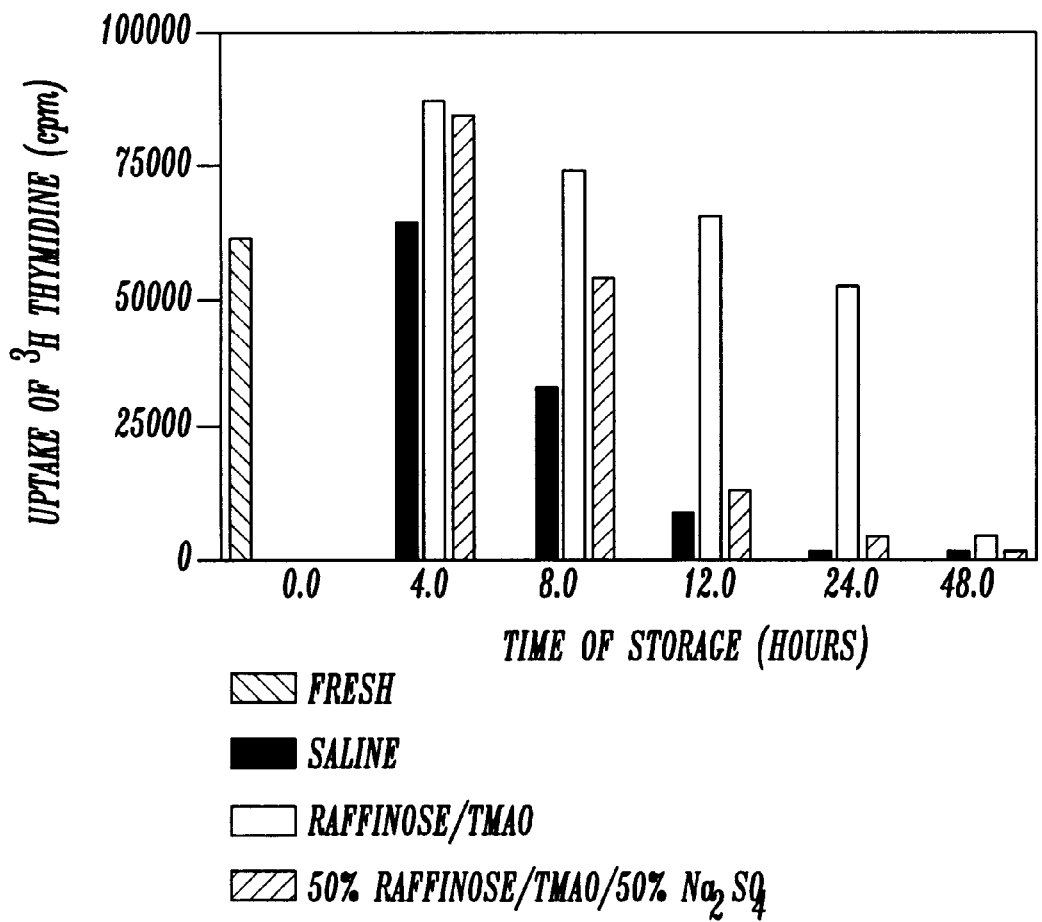
FIG. 21 shows proliferation of K562 chronic myelogenous leukemia cells assessed by uptake of tritiated thymidine following storage at 4° C. in saline or in preservation solutions of the present invention for up to 48 hours.

The efficacy of the inventive solutions for the preservation of various tumor cell lines, including the human lymphocytic leukemia Jurkat and K562 chronic myelogenous leukemia cell lines, at 4° C. was tested using the solutions tested for preservation of human bone marrow described above in Examples 5 and 6. FIGS. 20 and 21 show the proliferation of Jurkat and K562 cells, respectively, as assessed by uptake of tritiated thymidine, following storage at 4° C. in either saline or the inventive solutions. In contrast to the bone marrow progenitor cells, the tumor cell lines survived only two days in the inventive solutions before complete cell death. Thus, storage of bone marrow in the preservative solutions of the present invention at 4° C. for periods of greater than three days would purge the bone marrow of leukemic cells while maintaining the viability of the bone marrow.

EXAMPLE 9

The efficacy of the inventive solutions in the preservation of osteoblasts was demonstrated as follows.

Figure 22:
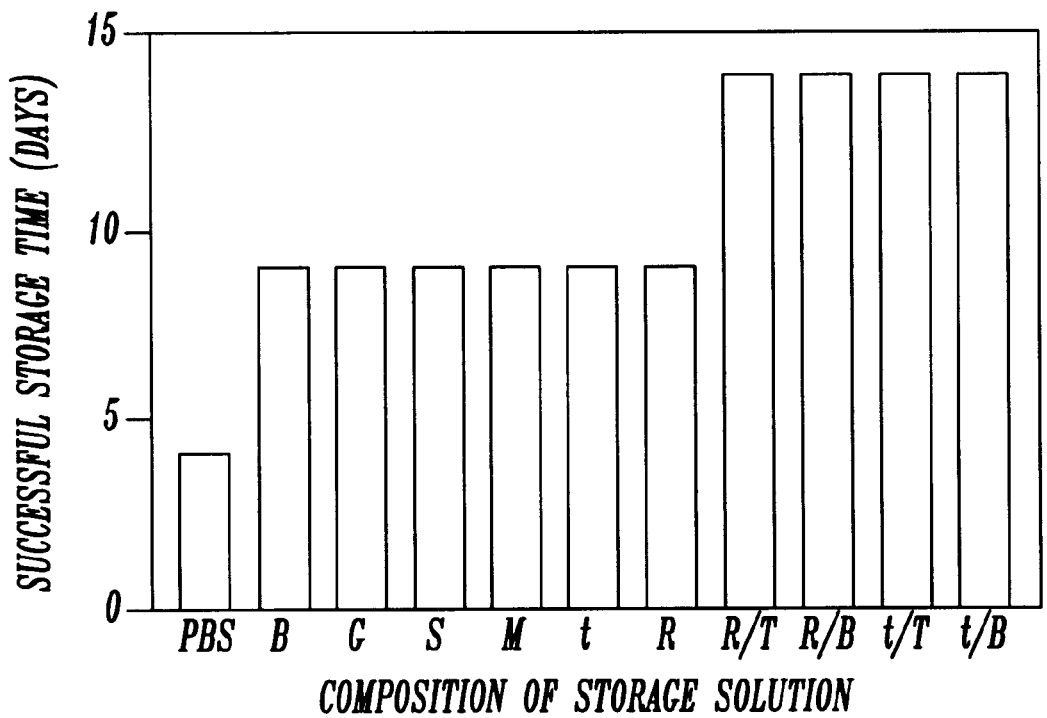
FIG. 22 shows proliferation to confluence of murine osteoblasts following storage at 4° C. in PBS and various preservation solutions of the present invention.

Mouse osteoblasts were dissected out and grown to near confluence in D-MEM culture medium at 38° C. They were then dispersed with trypsin in a $Ca^{2+}$- and $Mg^{2+}$-free phosphate buffered saline and re-seeded into D-MEM. After further culture, the medium was removed by aspiration and replaced with one of the following solutions: PBS, betaine, galactose, sorbitol, mannose, trehalose, raffinose, raffinose/TMAO (ratio 1.6:1), raffinose/betaine (ratio 1.6:1), trehalose/TMAO (ratio 1.6:1) and trehaloselbetaine (ratio 1.6:1). After storage at 4° C. for varying time intervals, the storage solution was aspirated off and replaced with D-MEM. A successful storage was one in which osteoblasts subsequently grew to confluence. As shown in FIG. 22, osteoblasts survived storage in the inventive solutions for much longer periods than in PBS. Osteoblasts were found to be more tolerant of fluctuations in osmolality than were embryos.

EXAMPLE 10

Figure 23:
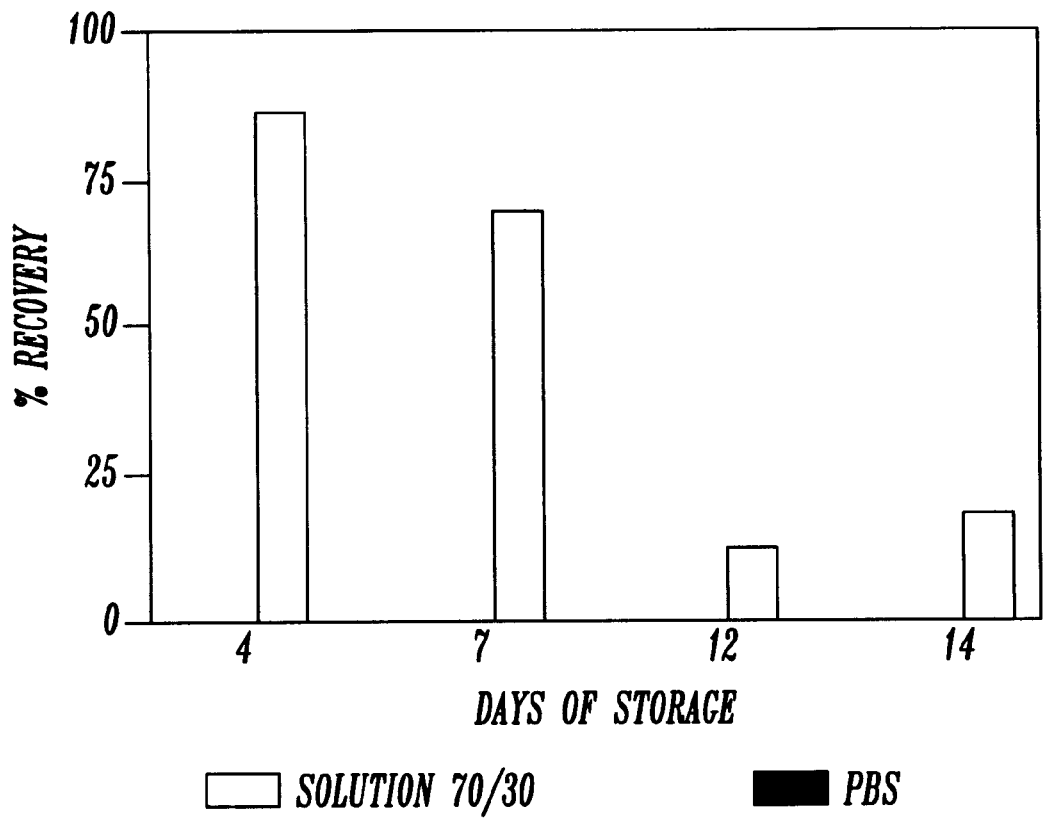
FIG. 23 shows the percentage recovery of a murine keratocyte cell line T7T after storage in PBS or Solution 70/30.

The efficacy of the inventive solutions in the preservation of murine T7T keratinocyte tumor cells was investigated as follows. The culture medium was removed from adherent cultures of T7T growing in D-MEM supplemented with 5% serum by aspiration and replaced with PBS or Solution 70/30 prior to storage at 4° C. After 4, 7, 12 and 14 days these solutions were removed, the adherent cells removed by trypsinization and recovery determined. FIG. 23 shows that no viable T7T cells survived in PBS but viable T7T cells were recovered following up to 14 days of storage in Solution 70/30.

EXAMPLE 11

The efficacy of the inventive solutions in the preservation of murine 3T3 fibroblast cells was demonstrated as follows.

Figure 24:
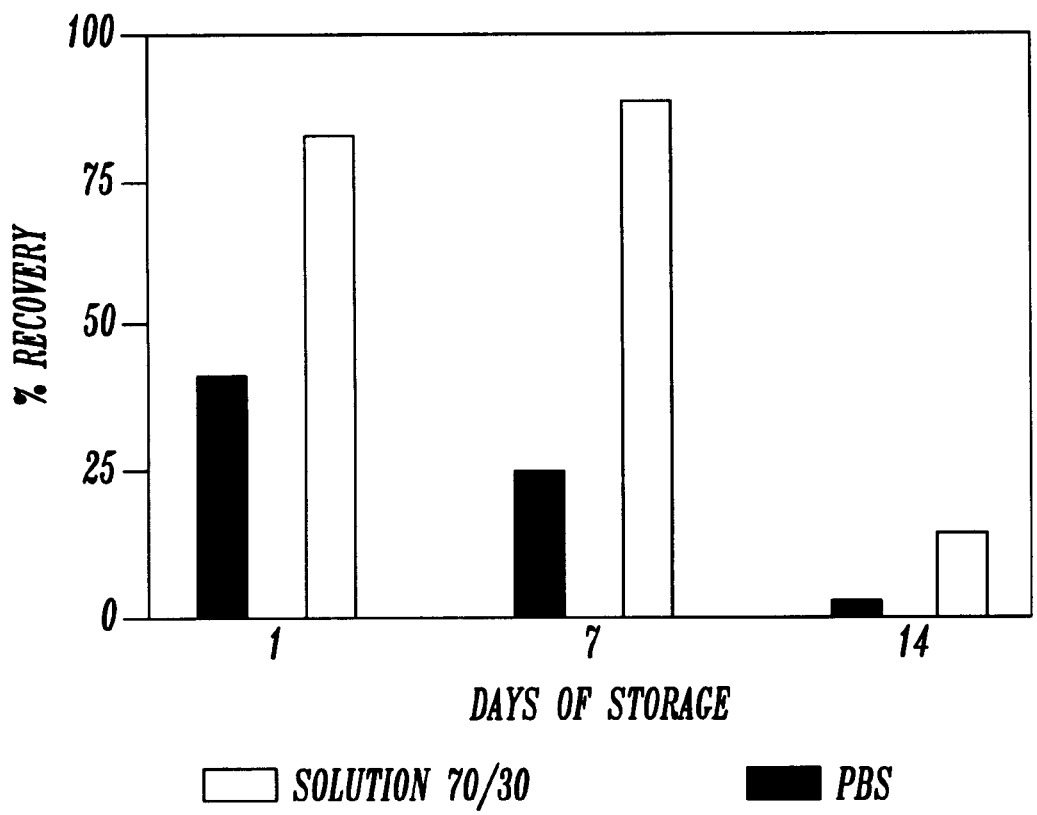
FIG. 24 shows the percentage recovery of murine 3T3 fibroblasts after storage in PBS or Solution 70/30.
Figure 25A:
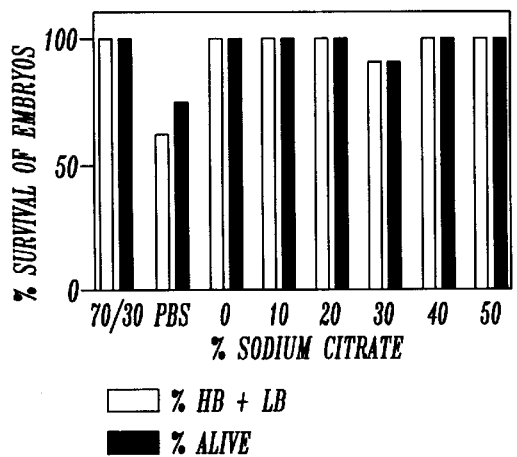
FIGS. 25A, B, C and D show the survival of mouse embryos following storage at 4° C. for 1, 2, 3 or 4 days, respectively, in either PBS, Solution 70/30 or a mixture of raffinose, TMAO, sodium citrate and calcium chloride.
Figure 25B:
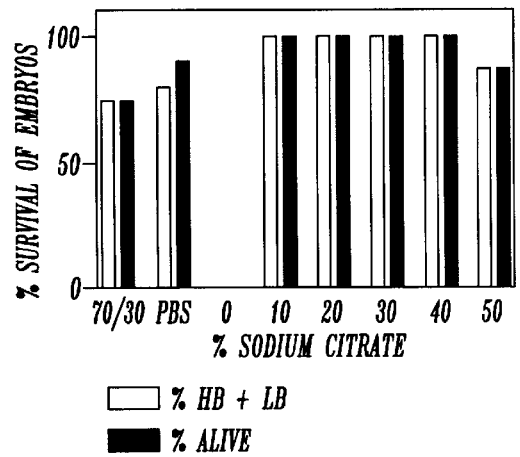
Figure 25C:
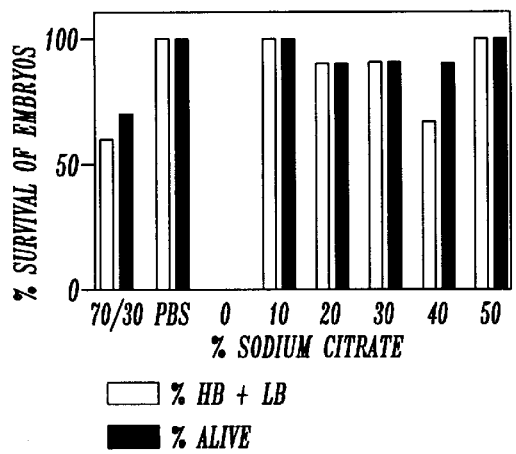
Figure 25D:
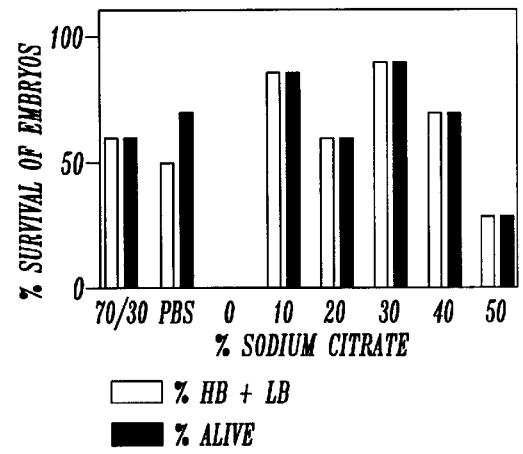
Figure 26A:
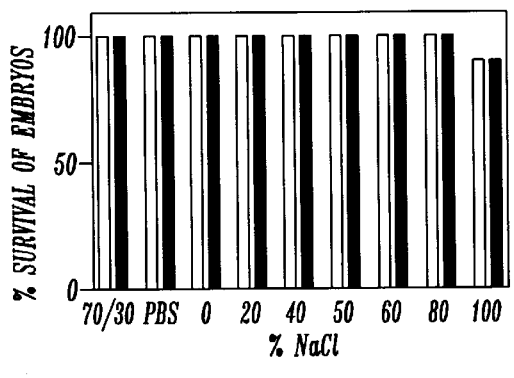
FIGS. 26A, B, C, D and E show the survival of mouse embryos following storage at 4° C. for 1, 2, 3, 4 or 5 days, respectively, in a range of mixtures of NaCl and TMAO plus calcium chloride.
Figure 26B:
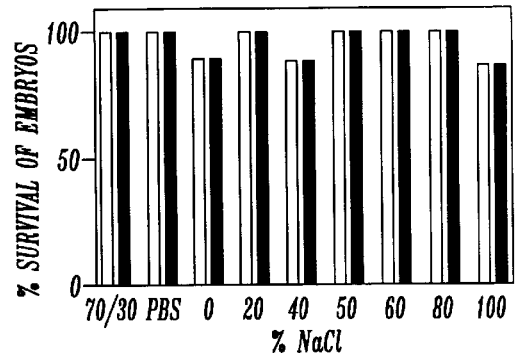
Figure 26C:
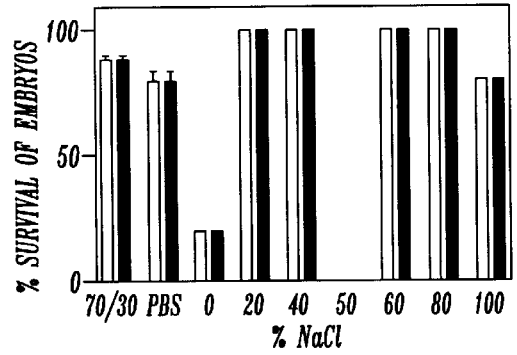
Figure 26D:
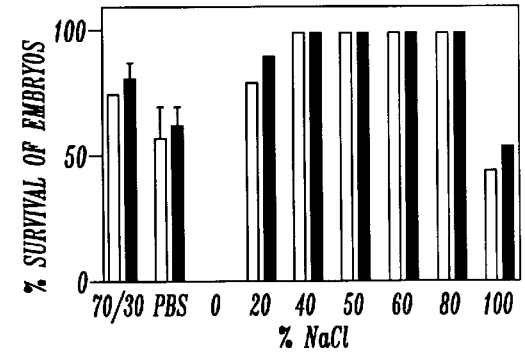
Figure 26E:
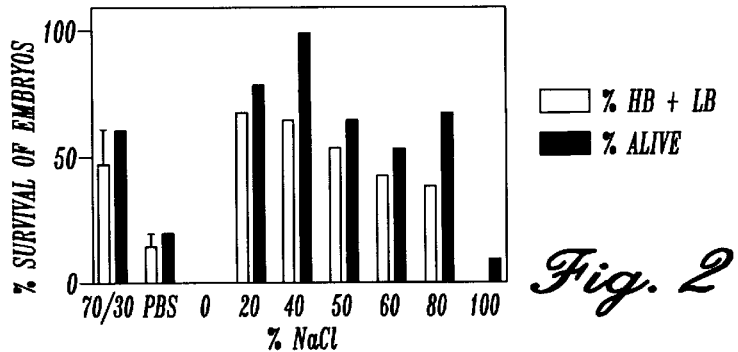

Adherent cultures of 3T3 cells growing in D-MEM supplemented with 5% serum had the medium removed by aspiration and replaced with PBS or Solution 70/30 prior to storage at 4° C. After 1, 7 and 14 days, these solutions were removed, the adherent cells were removed by trypsinization and recovery was determined. As shown in FIG. 24, no viable 3T3 cells survived in PBS but viable 3T3 cells were recovered after up to 14 days of storage in Solution 70/30.

EXAMPLE 12

This example illustrates the effectiveness of the inventive solutions in the preservation of platelets at temperatures below freezing.

Living cells are typically frozen slowly in solutions containing high concentrations (approximately 10% by volume) of cryoprotectants such as dimethylsulphoxide (DMSO). A programmed freezer takes the temperature down at a controlled rate until all water is assumed to be frozen, at which time the cells are plunged into liquid nitrogen. Thawing is also conducted relatively slowly. This is a tedious and expensive process with the serious disadvantage that DMSO is toxic to cells.

Figure 33A:
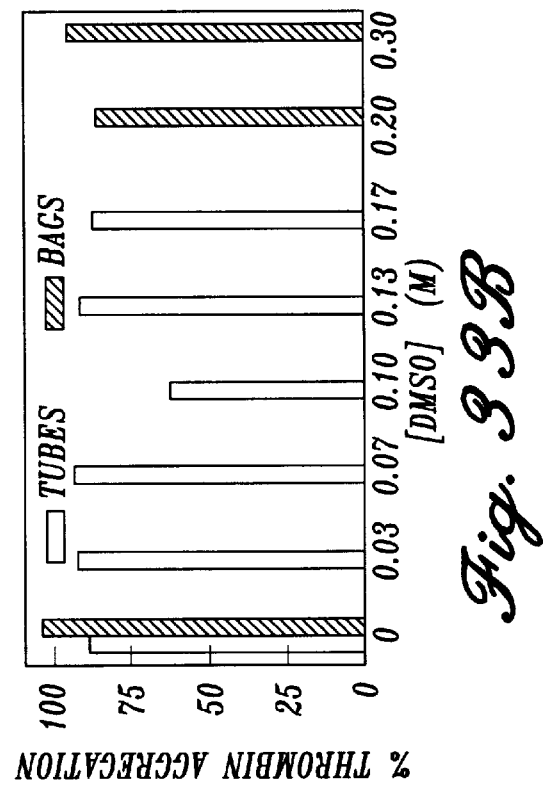
FIGS. 33A and B show the percentage thrombin-activated aggregation of platelets stored in either plasma or Solution 70/30C2, respectively, both solutions containing graded concentrations of DMSO, in either coated tubes or bags. Platelets were rapidly frozen at –140° C., and rapidly thawed at 37° C. in a water bath.
Figure 33B:
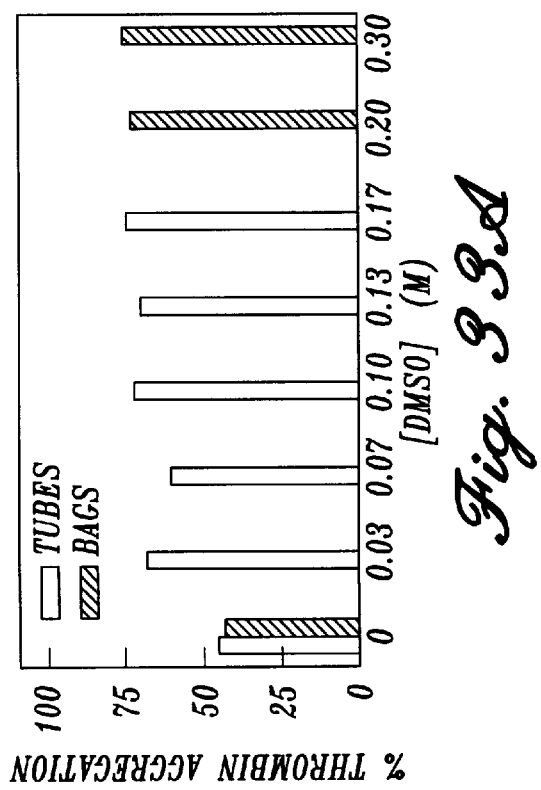

In contrast, cells placed in the inventive solutions were plunged into liquid nitrogen or placed in a freezer at −140° C. to lower the temperature as quickly as possible. They were also thawed as quickly as possible in a 37° C. water bath. FIGS. 33A and B show the success of this method with platelets. Platelets were suspended in plasma or Solution 70/30c2 contained either in freezing bags or in coated glass tubes. Graded concentrations of DMSO were added to the solutions. Tubes and bags were placed at −140° C. for 6 days. They were then thawed rapidly and assayed for platelet numbers and thrombin aggregation. Surface effects were found to be negligible in freezing since results for tubes and bags lay on continuous curves. In these studies, the best results were obtained with Solution 70/30c2 without added DMSO. This gave an average of nearly 100% thrombin aggregation and 50% recovery of platelets. Added DMSO made little difference. Even plasma, with this rapid freezing and thawing technique, gave nearly 50% aggregation without DMSO; this increased with added DMSO to nearly 100%. The concentration of DMSO added to achieve this level of thrombin aggregation was only about one fifth of the concentration normally used.

This method of freezing has many advantages: it uses no toxic compounds, does not require expensive equipment and, as shown below, can be successfully employed even with cells which are difficult to recover from freezing.

While not wishing to be bound by theory, applicants believe that the above techniques are effective due to the fact that cells normally contain separated populations of high and low density water which behave differently from normal water as the temperature falls. High density water has a very low freezing point (below −80° C.) and remains liquid and highly reactive during the slow freezing and thawing processes. It is therefore very damaging to cells, which mostly die. Low density water also does not freeze but passes from a low density inert liquid into a low density inert glassy solid. No ice is formed. When cells are plunged into liquid nitrogen they pass so rapidly through the temperature range in which high density water is still liquid and reactive, that there is insufficient time for cell damage to occur. Again, with rapid thawing, cells pass quickly through this dangerous temperature range. The other requirement for successful freezing and thawing is that ion channels are kept closed. This is achieved by using the inventive preservative solutions, rather than saline-based solutions.

In subsequent studies, the effectiveness of Solution 70/30c2 in the preservation of platelets was compared with that of a solution of betaine, sodium chloride and sodium citrate. Platelets were prepared by centrifugation of a 500 ml bag of blood collected in citrate anticoagulant at 1600 g for 7 minutes to give 176 ml platelet-rich plasma, which was centrifuged again at 2900 g for 13 minutes. The resulting platelet buttons were resuspended in either Solution 70/30c2 or a solution of 187 mM betaine, 45.8 mM sodium chloride and 1.96 mM sodium citrate before being rapidly frozen at −140° C. After storage, platelets were thawed rapidly at 37° C. Platelets stored for two and three days in the betaine/sodium chloride/sodium citrate solution showed 61% and 74% recovery, respectively, compared to 50% recovery in Solution 70/30c2. Platelets stored in the betaine/sodium chloride/sodium citrate solution responded to thrombin activation more slowly than platelets stored in Solution 70/30c2. However, when platelets taken from either solution are resuspended in plasma and incubated at 37° C., they take up glucose and acidify the extracellular solution, demonstrating that they are metabolically active.

Figure 37B:
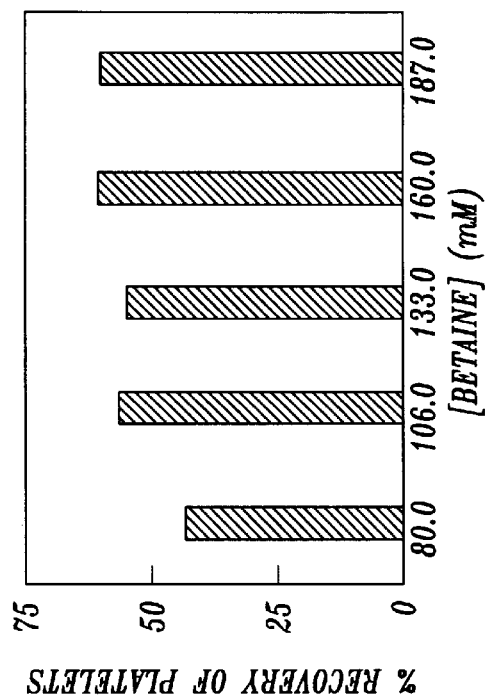
FIGS. 37A, B and C show platelet counts, percentage recovery of platelets, and percentage thrombin-activated aggregation, respectively, following storage at −140° C. and rapid thawing at 37° C., in solutions of NaCl, sodium citrate and varying concentrations of betaine.
Figure 37C:
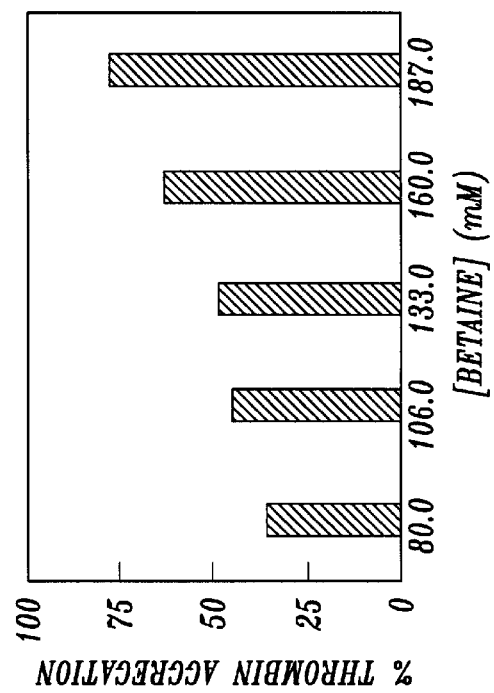
Figure 37A:
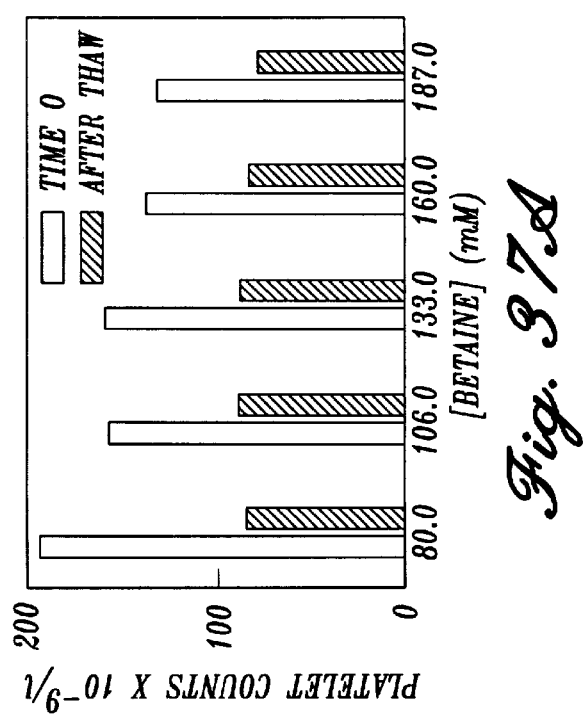

The effect of varying the concentration of betaine on the storage of platelets at temperatures below freezing was examined as follows. Solutions of betaine, NaCl and sodium citrate, having varying concentrations of betaine and NaCl were prepared as discussed above in Example 4. Platelets were prepared as described above, resuspended in the betaine/NaCl/sodium citrate solutions and rapidly frozen at −140° C. Following storage for 2 to 6 days, platelets were rapidly thawed at 37° C. Platelet counts, percentage recovery and percentage thrombin-activated aggregation following storage in solutions of varying betaine concentration are shown in FIGS. 37A, B and C, respectively. The highest percentage recoveries were obtained with the solution containing the highest concentration of betaine, which also appeared to have the highest percentage thrombin-activated aggregation. It should be noted that thrombin-activated aggregation is sometimes so slow in these solutions that the end-point is not reached during the normal timing of the process. This appears to be reversible and is probably due to the stabilization of the lipid bilayer by betaine.

EXAMPLE 13

This example illustrates the effectiveness of the inventive solutions and methods in the storage of Jurkat cells at temperatures below freezing.

Figure 34B:
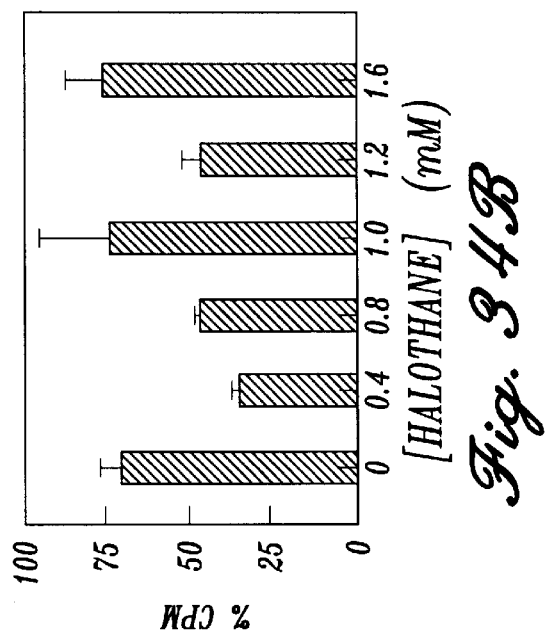
FIGS. 34A and B show the percentage viability and uptake of tritiated thymidine as a percentage of their uptake before freezing, respectively, by Jurkat cells frozen in Solution 70/30B. Cells were rapidly frozen at −140° C., and rapidly thawed at 37° C. in a water bath. Halothane was added at the concentrations shown before centrifugation of the cells and their uptake into Solution 70/30B. No cells survived similar treatment in PBS.
Figure 34A:
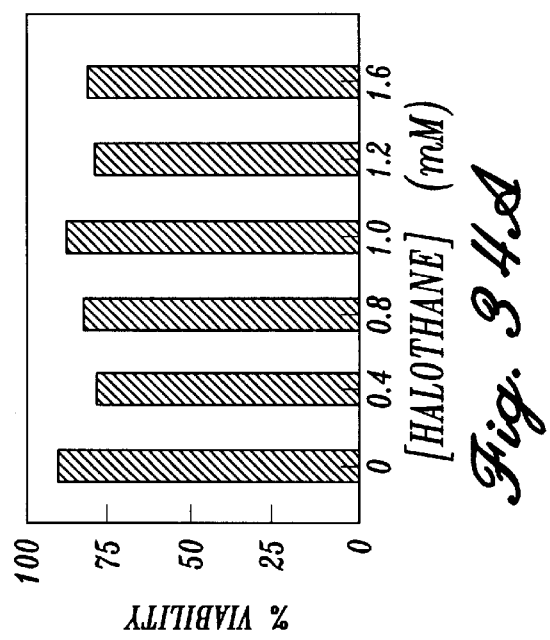

Jurkat cells are a human tumour cell line which is known to be difficult to freeze. Jurkat cells are typically frozen in 10% DMSO and 90% fetal calf serum. Even then, the percentage recovery is often low. When frozen in plasma without DMSO, all Jurkat cells die. Similarly, when frozen slowly in Solution 70/30B they all die. FIGS. 34A and B show the percentage recovery of viable cells and cell proliferation, as measured by percentage uptake of tritiated thymidine, respectively, of Jurkat cells rapidly frozen in Solution 70/30B at −140° C. and rapidly thawed at 37° C. in a water bath. Halothane was added in various concentrations before separation of the cells from their growth medium by centrifugation, in an attempt to protect cells from centrifugation damage. It can be seen, however, that this protection was not necessary: with no halothane recovery of viable cells was nearly 100% and of these thymidine uptake was nearly 75% of that before freezing.

Figure 35:
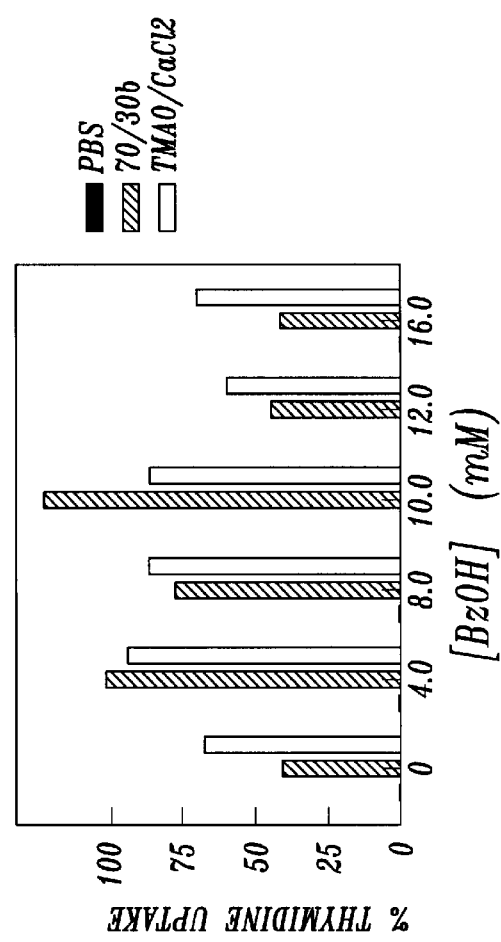
FIG. 35 shows the uptake of tritiated thymidine, as a percentage of uptake before freezing, by Jurkat cells which were rapidly frozen at −140° C. and rapidly thawed at 37° C. in either PBS, Solution 70/30B or TMAO (0.29 OsM) containing 1.75 mM $CaCl_2$. Benzyl alcohol was added to the suspensions before centrifugation and uptake in freezing solution in an attempt to protect the cells from centrifugation damage.

FIG. 35 shows the results of an experiment in which Jurkat cells were protected from centrifugation damage by addition of benzyl alcohol. The cells were rapidly frozen at −140° C. in either PBS, Solution 70/30B or trimethylamine oxide (0.29M OsM) containing 1.75 mM $CaCl_2$, and rapidly thawed at 37° C. In this experiment, in which the cells were in a poorer metabolic state before centrifugation, the added alcohol appeared to have a beneficial effect at low concentrations.

These results clearly demonstrate that the use of rapid freezing and thawing techniques in combination with the inventive preservative solutions is highly effective in the preservation of living biological materials at temperatures below freezing.

EXAMPLE 14

This example illustrates the lack of growth of microorganisms in the inventive solutions.

For effective storage of living biological materials, it is preferred that micro-organisms not grow in the preservative solution. Suspensions of platelets in Solution 70/30c2 were spiked with two micro-organisms which are known to grow at 4° C. in nutrient broth (*Yersinia enterocolitica* and *Listeria monocytogenes*). Platelets and microorganisms were then stored at 4° C. for three weeks. As shown in FIG. 32, neither of the two organisms showed sustained growth.

Although the present invention has been described in terms of specific embodiments, changes and modifications can be carried out without departing from the scope of the invention which is intended to be limited only by the scope of the appended claims.

We claim:

1. A solution for the preservation of living biological materials comprising betaine, sodium citrate and sodium chloride, the solution being isotonic with the material to be preserved and being substantially free of iodide, dihydrogen phosphate, bicarbonate, nitrate and bisulfate.

2. The solution of claim 1 additionally comprising calcium chloride.

3. The solution of claim 1, wherein the betaine is present at a concentration of about 150 mM to about 220 mM, the sodium citrate is present at a concentration of about 1.5 mM to about 2.5 mM and the sodium chloride is present at a concentration of about 35 mM to about 55 mM.

4. The solution of claim 1, wherein the living biological material to be preserved is a mammalian material and the solution has an osmolality of about 280 mOsM to about 320 mOsM.

5. The solution of claim 1, wherein the living biological material to be preserved is a plant material and the solution has an osmolality of about 70 mOsM to about 80 mOsM.

6. The solution of claim 1, wherein the living biological material to be preserved is a marine material and the solution has an osmolality of about 900 mOsM to about 1000 mMOsM.

7. A concentrated liquid solution that, upon addition of an aqueous liquid, forms a solution according to claim 1.

8. A collection of solids that, upon addition of an aqueos liquid, forms a solution according to claim 1.

9. A method for preserving the viability of a living biological material, comprising contacting the material with a solution according to claim 1.

10. A method for preserving the viability of a living biological material, comprising:
 (a) contacting the biological material with a solution according to claim 1; and
 (b) maintaining the biological material at a temperature less than about 4° C.

11. A method for preserving the viability of a living mammalian biological material, comprising:
 (b) contacting the biological material with a solution according to claim 4; and
 (c) maintaining the biological material at a temperature less than about 4° C.

12. The method of claim 11, wherein the living mammalian biological material is selected from the group consisting of organs, tissues and cells.

13. The method of claim 12 wherein the living mammalian biological material is selected from the group consisting of: heart, kidney, lung, liver, stem cells, bone marrow, embryos, whole blood, platelets, granulocytes, red blood cells, dendritic cells, oocytes, osteoblasts and skin cells.

14. The method of claim 11, wherein the biological material is maintained at a temperature less than about 0° C.

15. A method for preserving the viability of a living plant biological material, comprising:
 (a) contacting the biological material with a solution according to claim 5; and
 (b) maintaining the biological material at a temperature less than about 4° C.

16. The method of claim 15, wherein the biological material is maintained at a temperature less than about 0° C.

17. A method for preserving the viability of a living marine biological material, comprising:
 (a) contacting the biological material with a solution according to claim 6; and
 (b) maintaining the biological material at a temperature less than about 4° C.

18. The method of claim 17, wherein the biological material is maintained at a temperature less than about 0° C.

19. A method for preserving the viability of a biological material, comprising
 (a) contacting the biological material with a solution according to claim 1; and
 (b) lowering the temperature of the biological material and solution to a temperature of about −80° C. or lower and thereby freezing the biological material and solution.

20. The method of claim 19 wherein the temperature of the biological material is lowered to a temperature of about −140° C.

21. The method of claim 19 additionally comprising rapidly thawing the frozen biological material and solution.

22. The method of claim 19 wherein the solution is substantially free from conventional cryoprotectants.

23. A method for preserving the viability of a biological material at freezing temperatures in the absence of conventional cryoprotectants, comprising:
 (a) contacting the biological material with a solution according to claim 1;
 (b) rapidly lowering the temperature of the biological material and solution to a temperature of about −80° C. or lower and thereby freezing the biological material and solution.

24. The method of claim 23 wherein the temperature of the biological material is lowered to a temperature of about −140° C. or lower.

25. The method of claim 23 additionally comprising rapidly thawing the frozen biological material and solution.

* * * * *